US006887481B1

(12) United States Patent
Chan et al.

(10) Patent No.: US 6,887,481 B1
(45) Date of Patent: May 3, 2005

(54) BACTERIAL-DERIVED MOLECULES AND THERAPEUTIC AND DIAGNOSTIC USES THEREFOR

(75) Inventors: Lily Chan, Singapore (SG); Maxey Ching Ming Chung, Singapore (SG); Renee Lay Hong Lim, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 09/461,774

(22) Filed: Dec. 15, 1999

Related U.S. Application Data

(60) Provisional application No. 60/112,499, filed on Dec. 16, 1998.

(51) Int. Cl.$^7$ ........................ A61K 39/04; A61K 39/02; A61K 39/00

(52) U.S. Cl. .................. 424/248.1; 424/9.2; 424/130.1; 424/139.1; 424/141.1; 424/163.1; 424/164.1; 424/168.1; 424/9.1; 424/184.1; 424/185.1; 424/190.1; 424/234.1; 435/7.1; 435/7.2; 435/7.32; 435/253.1; 435/501; 435/512; 435/513; 530/300; 530/350

(58) Field of Search ....................... 424/9.1, 9.2, 130.1, 424/139.1, 141.1, 163.1, 164.1, 168.1, 184.1, 185.1, 190.1, 294.1, 248.1; 435/7.1, 7.2, 7.32, 253.1; 436/501, 512, 573; 530/300, 350

(56) References Cited

PUBLICATIONS

Thybo, S., et al. "Humoral response to *Mycobacterium tuberculosis*–specific antigens in African tuberculosis patients with high prevalence of human immunodeficiency virus infection." Tubercle and Lung Disease. vol. 76. pp. 149–155, 1995.*

* cited by examiner

*Primary Examiner*—Rodney P Swartz
(74) *Attorney, Agent, or Firm*—Birch, Stewart Kolasch & Birch LLP

(57) ABSTRACT

The present invention relates generally to molecules derived from a *Mycobacterium* species and recombinant, synthetic, derivative, homologue and analogue forms of said molecules. The molecules of the present invention are useful in diagnostic assays for *Mycobacterium* in biological and environmental samples. The present invention is particularly directed to molecules derived from *Mycobacterium tuberculosis* and related organisms and even more particularly to recombinant forms of these molecules or synthetic, derivative, homologue or analogue forms thereof and their use in diagnostic and therapeutic protocols for tuberculosis or other disease conditions associated with *M. tuberculosis* or related organisms.

21 Claims, 9 Drawing Sheets

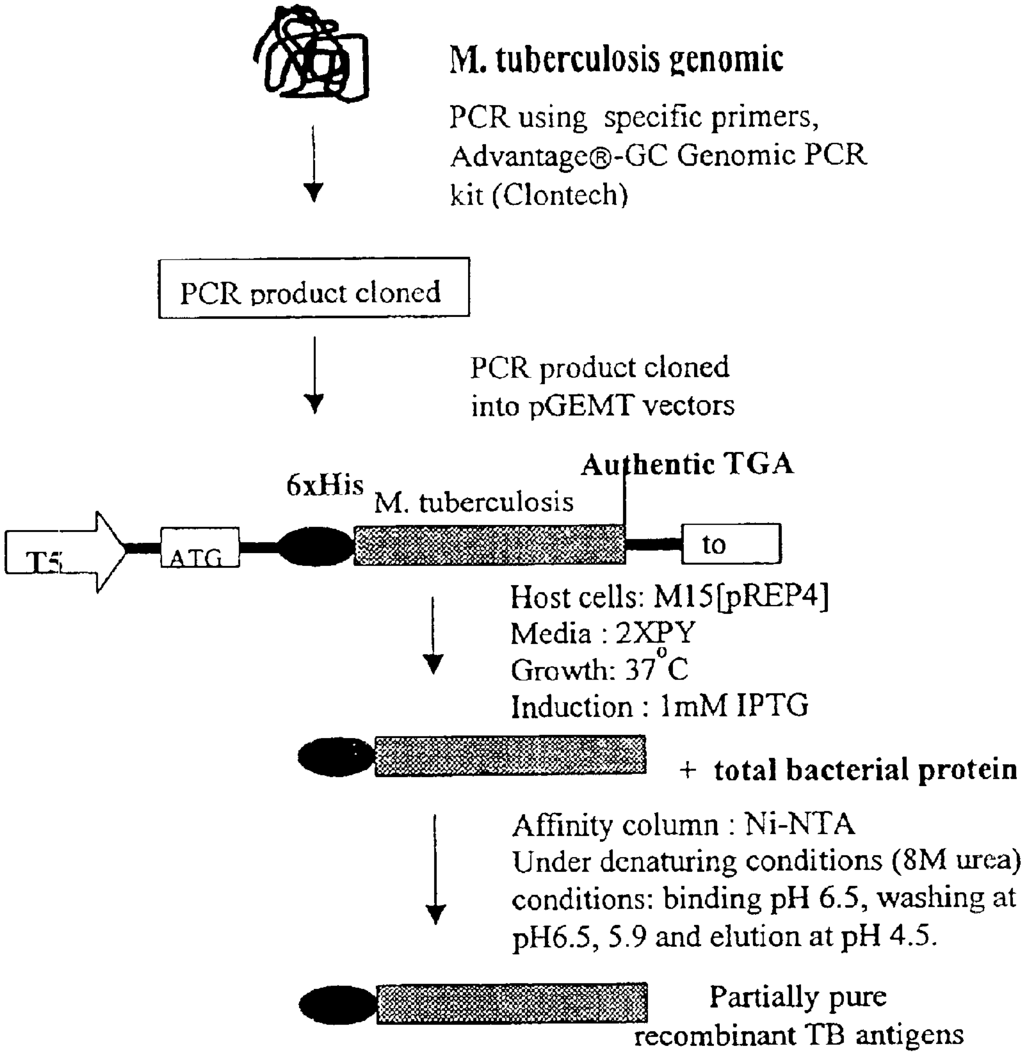
Fig.1 Strategy for the isolation and expression of M.tuberculosis protein antigens.

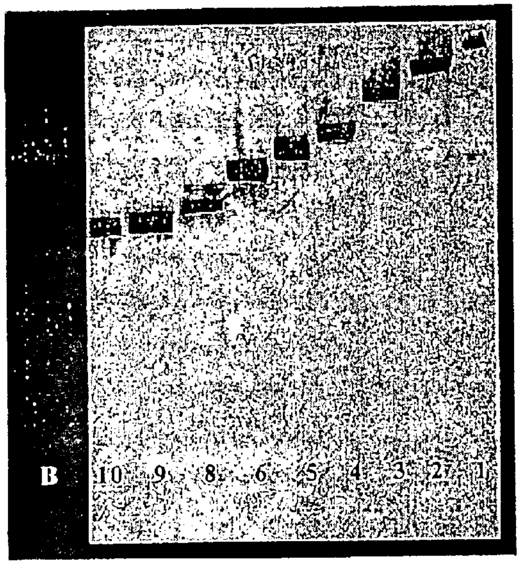
(A)
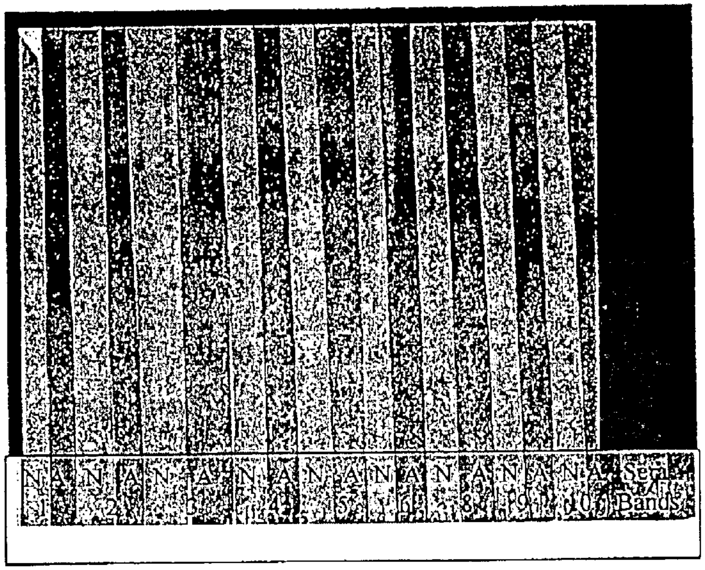
(B)
Fig.2. (A) Gel purified and concentrated M. tuberculosis protein bands (B.1, 2, 3, 4, 5, 6, 8, 9, 10) blotted onto PVDF membrane were excised for N-terminal sequencing. (B) Concentrated M. tuberculosis protein bands blotted onto nitrocellulose membrane and immuno-screened using pooled normal (N) and active (A) sera respectively. Positive bands (arrows) were observed with A but not with N.

Fig. 3 Result of homology search against the GenBank protein sequence databases. Proteins showing the highest homology to the M. tuberculosis protein bands are as shown.

| Relative molecular weight (kDa) | Sequence from N-terminal sequencing | Match (GenBank) |
|---|---|---|
| B.4 | SKLIEYDELALEAME | db: $_2$SKLIEYDETARHAME$_{16}$ 55.74kDa, groEL1/protein cpn60 [16], pID=g44601, X60350 (80% match) |
| B.5 | AKTIAYDEEARV | db: $_2$AKTIAYDEEA$_{10}$ 56.728 kDa, CHAPERONIN2, groEL2, GenBank pID=g15000, MTTCWPA_3 (100% match) |
| B.6 | AEVDAYKFDPDAVD | db: $_{161}$AEFDAYRRDPMA$_{172}$ Probable exported protease, has signal sequence, very similar to three proteases / peptidases from Streptomyces, pID=e235164, MTCY427.04c (51% match) |
| B.9 | AEYTLPDLDWDYG | db: $_2$AEYTLPDLDWDYG$_{14}$ 23.0 kDa, superoxide dismutase, pID=g581379, MTSOD4 (100% match) |
| B.10 | MEIDILAVAAP | db: $_{117}$IEVDLLDLDAP$_{127}$ 33 kDa, mycocerosic acid synthase [17], pID=g149978, M95808 (56.9% match) |
| MMP | ATTLPVQRHDARL | db:ATLPVQRHPRSL 14/16 kDa [18], pID=g244562, M76712 |

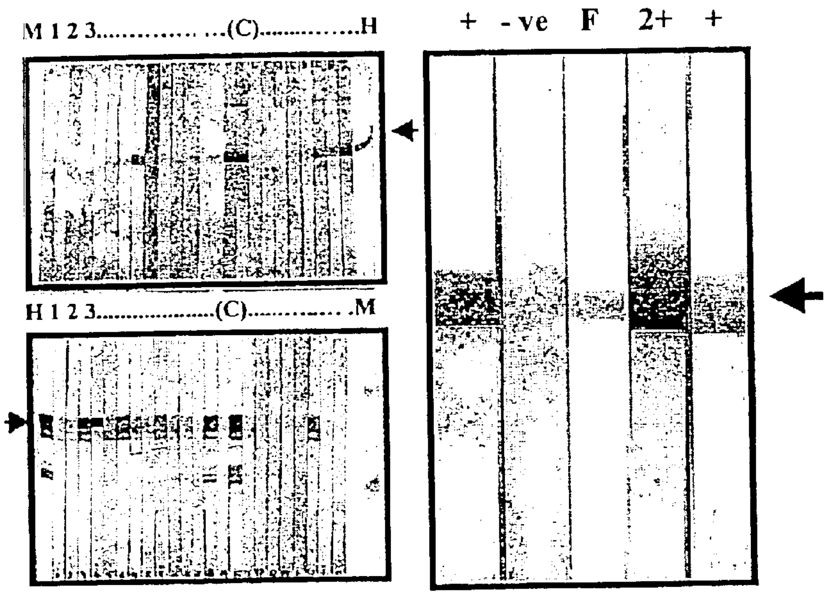

(A) (B)

Fig. 4. Western screening of recombinant M. tuberculosis antigens. (A) Arrows indicate the position of the recombinant antigens on the membrane. M= Kaleidoscope protein Marker and H= strip probed with anti-RGSHis, C= a positive control of strips probed with known human serum reactive to the specific recombinant antigen. (B) Reactivity is estimated based on the intensity of band on

Fig 5. Percentage of reactivity of recombinant TB antigens against different sera panels. A known 38kDa antigen [20, 21] of M. tuberculosis was included in the screening. The gene (GeneBank Accession # M30046) for this antigen was cloned, expressed in pQE30 and partially purified as described in section E. Also shown are the percentage of reactivity of sera samples detected by a commercially available rapid TB diagnostic kit from ICT (Amrad).

| Sera Panel:<br><br>Recombinant antigens: | Uninfected (normal) | Active TB (Extra-Pulmonary) | Active TB (Pulmonary) | Inactive |
|---|---|---|---|---|
| B.4 | 5% | 55% | 47.8% | 22.7% |
| B.5 | 25% | 35% | 39.1% | 27.3% |
| B.6 | 0% | 5% | 52.2% | 9.1% |
| B.9 | 0% | 25% | 17.4% | 18.2% |
| B.10 | 0% | 5% | 26.1% | 0% |
| MMP | 0% | 25% | 8.7% | 4.5% |
| C17 | 0% | 15% | 13.0% | 4.5% |
| 38 kDa | 0% | 40% | 39.1% | 18.2% |
| ICT TB Kit | 0% | 55% | 52.2% | 13.6% |

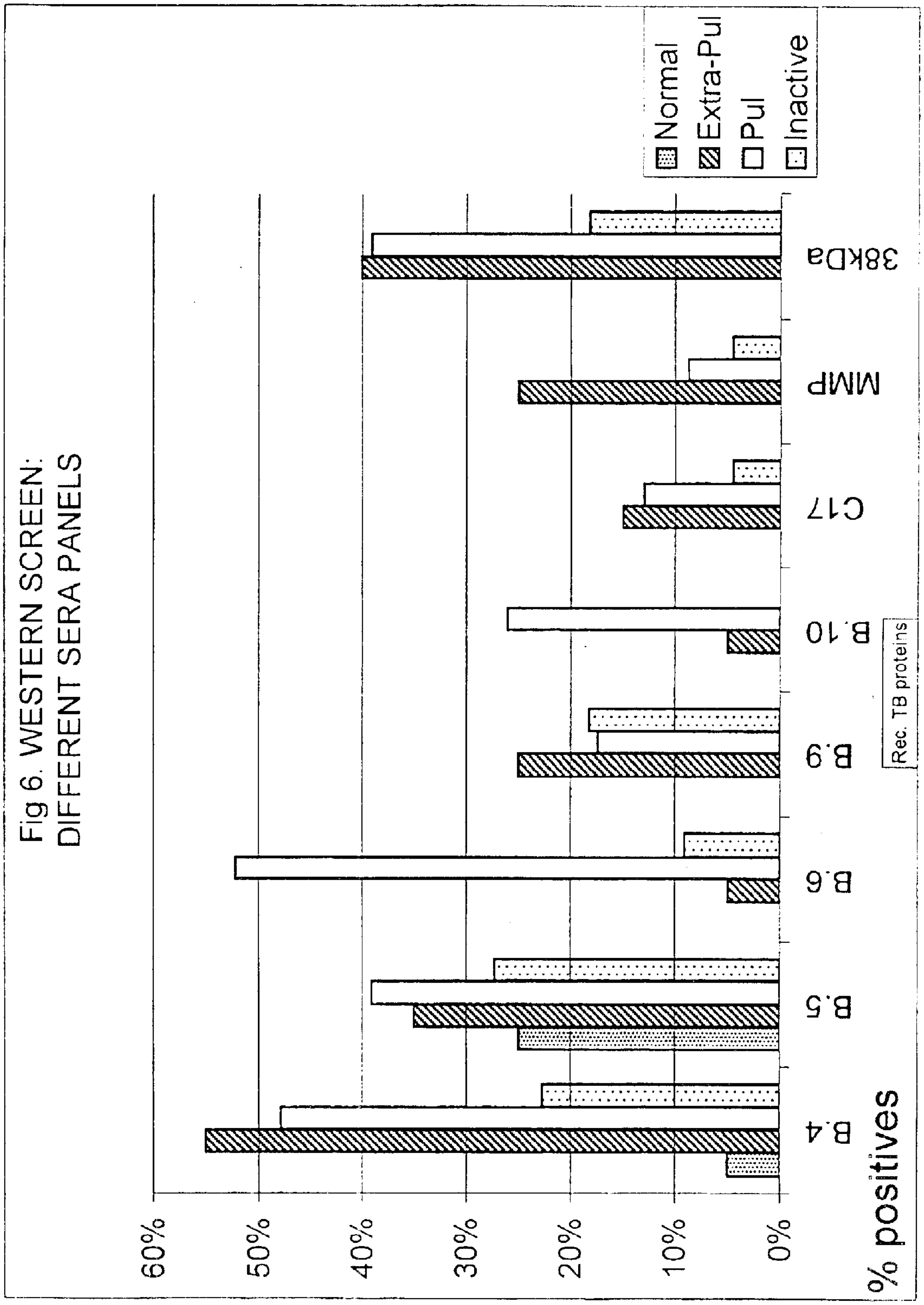
Fig 6. WESTERN SCREEN: DIFFERENT SERA PANELS

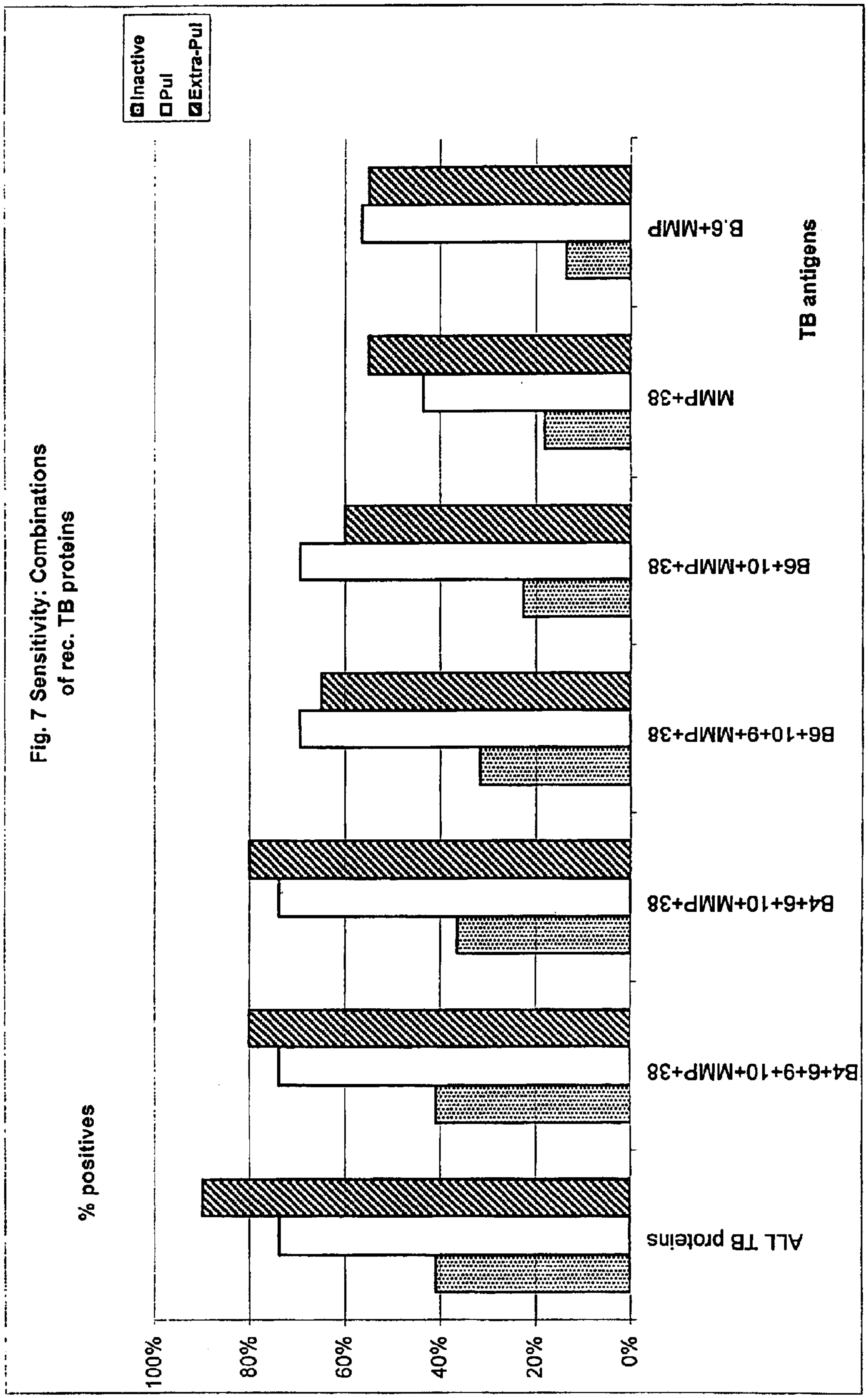
Fig. 7 Sensitivity: Combinations of rec. TB proteins

Fig. 8 Comparison of our rec. TB proteins with the ICT TB diagnostic kit
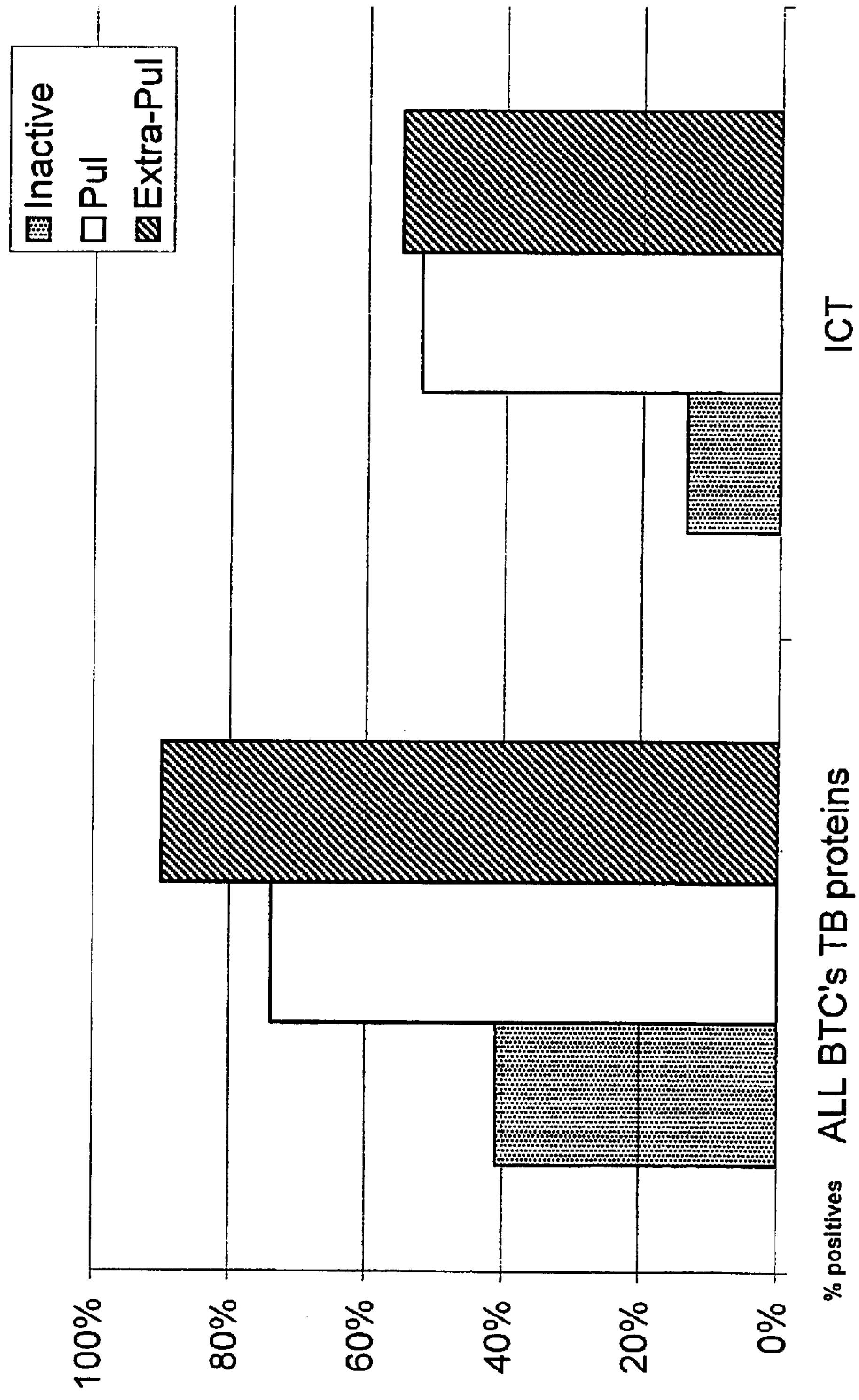

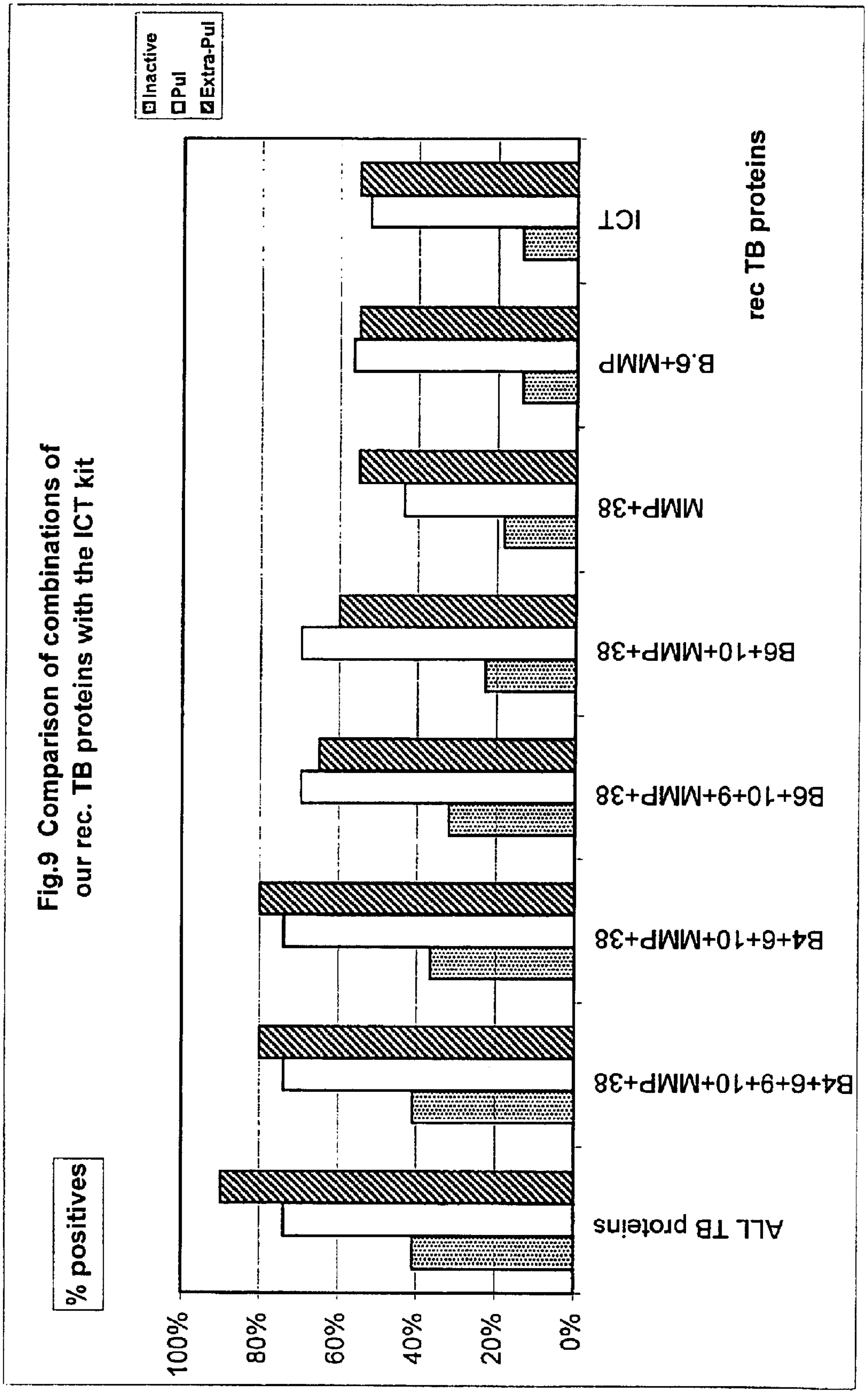
Fig.9 Comparison of combinations of our rec. TB proteins with the ICT kit

SEQUENCE LISTING

```
<160> NUMBER OF SEQ ID NOS: 22

<210> SEQ ID NO 1
<211> LENGTH: 1617
<212> TYPE: DNA
<213> ORGANISM: Mycobacterium tuberculosis
<220> FEATURE:
<221> NAME/KEY: CDS
<222> LOCATION: (1)..(1617)
```

-continued

```
<220> FEATURE:
<221> NAME/KEY: mat_peptide
<222> LOCATION: (1)..(1617)

<400> SEQUENCE: 1

agc aag ctg atc gaa tac gac gaa acc gcg cgt cgc gcc atg gag gtc        48
Ser Lys Leu Ile Glu Tyr Asp Glu Thr Ala Arg Arg Ala Met Glu Val
  1               5                  10                  15

ggc atg gac aag ctg gcc gac acc gtg cgg gtg acg ctg ggg ccg cgc        96
Gly Met Asp Lys Leu Ala Asp Thr Val Arg Val Thr Leu Gly Pro Arg
             20                  25                  30

ggc cgg cat gtg gtg ctg gcc aag gcg ttt ggc gga ccc acg gtt acc       144
Gly Arg His Val Val Leu Ala Lys Ala Phe Gly Gly Pro Thr Val Thr
         35                  40                  45

aac gac ggc gtc acg gtg gca cgt gag atc gag ctg gaa gat ccg ttt       192
Asn Asp Gly Val Thr Val Ala Arg Glu Ile Glu Leu Glu Asp Pro Phe
     50                  55                  60

gaa gac ttg ggc gcc cag ctg gtg aag tcg gtg gcc acc aag acc aac       240
Glu Asp Leu Gly Ala Gln Leu Val Lys Ser Val Ala Thr Lys Thr Asn
 65                  70                  75                  80

gat gtt gcc ggt gac ggc acc acc acc gca acc atc ttg gcg cag gca       288
Asp Val Ala Gly Asp Gly Thr Thr Thr Ala Thr Ile Leu Ala Gln Ala
                 85                  90                  95

ctg atc aag ggc ggc ctg agg cta gtg gcc gcc ggc gtc aac ccg gtc       336
Leu Ile Lys Gly Gly Leu Arg Leu Val Ala Ala Gly Val Asn Pro Val
            100                 105                 110

gcg ctc ggc gtg gga atc ggc aag gcc gcc gac gcg gta ttc gag gcg       384
Ala Leu Gly Val Gly Ile Gly Lys Ala Ala Asp Ala Val Phe Glu Ala
        115                 120                 125

ctg ctg gca tcg gcc acg ccg gtg tcc ggc aag acc ggc atc gcg cag       432
Leu Leu Ala Ser Ala Thr Pro Val Ser Gly Lys Thr Gly Ile Ala Gln
    130                 135                 140

gtg gcg acg gtg tcc tcg cgc gac gag cag atc ggt gac ctg gtt ggc       480
Val Ala Thr Val Ser Ser Arg Asp Glu Gln Ile Gly Asp Leu Val Gly
145                 150                 155                 160

gaa gcg atg aac aag gtc ggc cac gac agc gtg gtc agc gtc aag gaa       528
Glu Ala Met Asn Lys Val Gly His Asp Ser Val Val Ser Val Lys Glu
                165                 170                 175

tcc tcc acg ctg ggc acc gag ttg gag ttc acc gaa ggt att ggc ttc       576
Ser Ser Thr Leu Gly Thr Glu Leu Glu Phe Thr Glu Gly Ile Gly Phe
            180                 185                 190

cac aaa ggc ttc ttg tcg gca tac ttc gtt acc gac ttc gat aac cag       624
His Lys Gly Phe Leu Ser Ala Tyr Phe Val Thr Asp Phe Asp Asn Gln
        195                 200                 205

cag gcg gtg ctc gag gac gcg ttg atc ctg cta cac caa gac aag atc       672
Gln Ala Val Leu Glu Asp Ala Leu Ile Leu Leu His Gln Asp Lys Ile
    210                 215                 220

agc tcg ctt ccc gat ctg ttg cca ttg ctg gaa aag gtt gca gga acg       720
Ser Ser Leu Pro Asp Leu Leu Pro Leu Leu Glu Lys Val Ala Gly Thr
225                 230                 235                 240

ggt aag cca cta ctg atc gtg gct gaa gac gtg gag ggc gaa gcg ttg       768
Gly Lys Pro Leu Leu Ile Val Ala Glu Asp Val Glu Gly Glu Ala Leu
                245                 250                 255

gcg acg ctg gtc gtc aac gcg att cgc aag acg ttg aaa gcg gtc gcg       816
Ala Thr Leu Val Val Asn Ala Ile Arg Lys Thr Leu Lys Ala Val Ala
            260                 265                 270

gtc aag ggg ccg tac ttc ggt gac cgc cgt aag gcg ttc ctt gag gac       864
Val Lys Gly Pro Tyr Phe Gly Asp Arg Arg Lys Ala Phe Leu Glu Asp
        275                 280                 285

ctg gcg gtg gtg acg ggt ggc cac gtg gtc aac ccc gac gcc ggc att       912
```

-continued

```
Leu Ala Val Val Thr Gly Gly His Val Val Asn Pro Asp Ala Gly Ile
    290                 295                 300

gtg ctg cgc gag gtg ggc ttg gag gtg ctg ggc tcg gcc cga cgc gtg      960
Val Leu Arg Glu Val Gly Leu Glu Val Leu Gly Ser Ala Arg Arg Val
305                 310                 315                 320

gtg gtc agc aag gac gac acg gtc att gtc gac ggc ggc ggc acc gca     1008
Val Val Ser Lys Asp Asp Thr Val Ile Val Asp Gly Gly Gly Thr Ala
                325                 330                 335

gaa gcg gtg gcc aac cgg gcg aac cac ttg cgt gcc gag atc gac aag     1056
Glu Ala Val Ala Asn Arg Ala Asn His Leu Arg Ala Glu Ile Asp Lys
            340                 345                 350

agc gat tcg gat tgg gat cgg gaa aag ctt ggc gag cgg ctg gcc aaa     1104
Ser Asp Ser Asp Trp Asp Arg Glu Lys Leu Gly Glu Arg Leu Ala Lys
        355                 360                 365

ctg gcc ggc ggg gtt gct gtc atc aag gtg ggt gcc gcc acc gac acc     1152
Leu Ala Gly Gly Val Ala Val Ile Lys Val Gly Ala Ala Thr Asp Thr
    370                 375                 380

gca ctc aag gag cgc aag gaa agc gtc gag gat gcg gtc gcg gcc gcc     1200
Ala Leu Lys Glu Arg Lys Glu Ser Val Glu Asp Ala Val Ala Ala Ala
385                 390                 395                 400

aag gcc gcg gtc gag gag ggc atc gtc cct ggt ggg gga gcc tcg ctc     1248
Lys Ala Ala Val Glu Glu Gly Ile Val Pro Gly Gly Gly Ala Ser Leu
                405                 410                 415

atc cac cag gcc cgc aag gcg ctg acc gaa ctg cgt gcg tcg ctg acc     1296
Ile His Gln Ala Arg Lys Ala Leu Thr Glu Leu Arg Ala Ser Leu Thr
            420                 425                 430

ggt gac gag gtc ctc ggt gtc gac gtg ttc tcc gaa gcc ctt gcc gcg     1344
Gly Asp Glu Val Leu Gly Val Asp Val Phe Ser Glu Ala Leu Ala Ala
        435                 440                 445

ccg ttg ttc tgg atc gcc gcc aac gct ggc ttg gac ggc tcg gtg gtg     1392
Pro Leu Phe Trp Ile Ala Ala Asn Ala Gly Leu Asp Gly Ser Val Val
    450                 455                 460

gtc aac aag gtc agc gag cta ccc gcc ggg cat ggg ctg aac gtg aac     1440
Val Asn Lys Val Ser Glu Leu Pro Ala Gly His Gly Leu Asn Val Asn
465                 470                 475                 480

acc ctg agc tat ggt gac ttg gcc gct gac ggc gtc atc gac ccg gtc     1488
Thr Leu Ser Tyr Gly Asp Leu Ala Ala Asp Gly Val Ile Asp Pro Val
                485                 490                 495

aag gtg act agg tcg gcg gtg ttg aac gcg tca tcg gtt gcc cgg atg     1536
Lys Val Thr Arg Ser Ala Val Leu Asn Ala Ser Ser Val Ala Arg Met
            500                 505                 510

gta ctc acc acc gag acg gtc gtg gtc gac aag ccg gcc aag gca gaa     1584
Val Leu Thr Thr Glu Thr Val Val Val Asp Lys Pro Ala Lys Ala Glu
        515                 520                 525

gat cac gac cat cac cac ggg cac gcg cac tga                         1617
Asp His Asp His His His Gly His Ala His
    530                 535


<210> SEQ ID NO 2
<211> LENGTH: 538
<212> TYPE: PRT
<213> ORGANISM: Mycobacterium tuberculosis

<400> SEQUENCE: 2

Ser Lys Leu Ile Glu Tyr Asp Glu Thr Ala Arg Arg Ala Met Glu Val
  1               5                  10                  15

Gly Met Asp Lys Leu Ala Asp Thr Val Arg Val Thr Leu Gly Pro Arg
            20                  25                  30

Gly Arg His Val Val Leu Ala Lys Ala Phe Gly Gly Pro Thr Val Thr
        35                  40                  45
```

-continued

```
Asn Asp Gly Val Thr Val Ala Arg Glu Ile Glu Leu Glu Asp Pro Phe
     50                  55                  60

Glu Asp Leu Gly Ala Gln Leu Val Lys Ser Val Ala Thr Lys Thr Asn
 65                  70                  75                  80

Asp Val Ala Gly Asp Gly Thr Thr Thr Ala Thr Ile Leu Ala Gln Ala
                 85                  90                  95

Leu Ile Lys Gly Gly Leu Arg Leu Val Ala Ala Gly Val Asn Pro Val
            100                 105                 110

Ala Leu Gly Val Gly Ile Gly Lys Ala Ala Asp Ala Val Phe Glu Ala
        115                 120                 125

Leu Leu Ala Ser Ala Thr Pro Val Ser Gly Lys Thr Gly Ile Ala Gln
    130                 135                 140

Val Ala Thr Val Ser Ser Arg Asp Glu Gln Ile Gly Asp Leu Val Gly
145                 150                 155                 160

Glu Ala Met Asn Lys Val Gly His Asp Ser Val Val Ser Val Lys Glu
                165                 170                 175

Ser Ser Thr Leu Gly Thr Glu Leu Glu Phe Thr Glu Gly Ile Gly Phe
            180                 185                 190

His Lys Gly Phe Leu Ser Ala Tyr Phe Val Thr Asp Phe Asp Asn Gln
        195                 200                 205

Gln Ala Val Leu Glu Asp Ala Leu Ile Leu Leu His Gln Asp Lys Ile
    210                 215                 220

Ser Ser Leu Pro Asp Leu Leu Pro Leu Leu Glu Lys Val Ala Gly Thr
225                 230                 235                 240

Gly Lys Pro Leu Leu Ile Val Ala Glu Asp Val Glu Gly Glu Ala Leu
                245                 250                 255

Ala Thr Leu Val Val Asn Ala Ile Arg Lys Thr Leu Lys Ala Val Ala
            260                 265                 270

Val Lys Gly Pro Tyr Phe Gly Asp Arg Arg Lys Ala Phe Leu Glu Asp
        275                 280                 285

Leu Ala Val Val Thr Gly Gly His Val Val Asn Pro Asp Ala Gly Ile
    290                 295                 300

Val Leu Arg Glu Val Gly Leu Glu Val Leu Gly Ser Ala Arg Arg Val
305                 310                 315                 320

Val Val Ser Lys Asp Asp Thr Val Ile Val Asp Gly Gly Gly Thr Ala
                325                 330                 335

Glu Ala Val Ala Asn Arg Ala Asn His Leu Arg Ala Glu Ile Asp Lys
            340                 345                 350

Ser Asp Ser Asp Trp Asp Arg Glu Lys Leu Gly Glu Arg Leu Ala Lys
        355                 360                 365

Leu Ala Gly Gly Val Ala Val Ile Lys Val Gly Ala Ala Thr Asp Thr
    370                 375                 380

Ala Leu Lys Glu Arg Lys Glu Ser Val Glu Asp Ala Val Ala Ala Ala
385                 390                 395                 400

Lys Ala Ala Val Glu Glu Gly Ile Val Pro Gly Gly Gly Ala Ser Leu
                405                 410                 415

Ile His Gln Ala Arg Lys Ala Leu Thr Glu Leu Arg Ala Ser Leu Thr
            420                 425                 430

Gly Asp Glu Val Leu Gly Val Asp Val Phe Ser Glu Ala Leu Ala Ala
        435                 440                 445

Pro Leu Phe Trp Ile Ala Ala Asn Ala Gly Leu Asp Gly Ser Val Val
    450                 455                 460
```

-continued

```
Val Asn Lys Val Ser Glu Leu Pro Ala Gly His Gly Leu Asn Val Asn
465                 470                 475                 480

Thr Leu Ser Tyr Gly Asp Leu Ala Ala Asp Gly Val Ile Asp Pro Val
                485                 490                 495

Lys Val Thr Arg Ser Ala Val Leu Asn Ala Ser Ser Val Ala Arg Met
            500                 505                 510

Val Leu Thr Thr Glu Thr Val Val Val Asp Lys Pro Ala Lys Ala Glu
        515                 520                 525

Asp His Asp His His His Gly His Ala His
    530                 535


<210> SEQ ID NO 3
<211> LENGTH: 1560
<212> TYPE: DNA
<213> ORGANISM: Mycobacterium tuberculosis
<220> FEATURE:
<221> NAME/KEY: CDS
<222> LOCATION: (1)..(1560)
<220> FEATURE:
<221> NAME/KEY: mat_peptide
<222> LOCATION: (1)..(1560)

<400> SEQUENCE: 3

gcg gcc atg tgg cgc cgc aga ccg ttg agc tcg gcg ctg ctg tcc ttc       48
Ala Ala Met Trp Arg Arg Arg Pro Leu Ser Ser Ala Leu Leu Ser Phe
  1               5                  10                  15

ggg ttg ctg ctc ggc gga ctg ctc cta gca gcg ccc ccg ttg gcc ggc       96
Gly Leu Leu Leu Gly Gly Leu Leu Leu Ala Ala Pro Pro Leu Ala Gly
            20                  25                  30

gcg act gaa gaa ccc ggc gcc ggc caa acc ccg ggt gcg ccg gtc gtg      144
Ala Thr Glu Glu Pro Gly Ala Gly Gln Thr Pro Gly Ala Pro Val Val
        35                  40                  45

gcg ccg caa cag agt tgg aac agc tgc cgc gag ttc atc gcc gac acc      192
Ala Pro Gln Gln Ser Trp Asn Ser Cys Arg Glu Phe Ile Ala Asp Thr
     50                  55                  60

agc gaa att cgc act gca cgc tgc gcg acg gtg tcc gtc ccc gtc gac      240
Ser Glu Ile Arg Thr Ala Arg Cys Ala Thr Val Ser Val Pro Val Asp
 65                  70                  75                  80

tac gac caa ccc ggt ggg aca caa gcg aag ttg gcg gtg atc cgc gtc      288
Tyr Asp Gln Pro Gly Gly Thr Gln Ala Lys Leu Ala Val Ile Arg Val
                 85                  90                  95

ccc gcg acg gga cag cga ttc gga gca ctg ctg gtc aat cct ggg gga      336
Pro Ala Thr Gly Gln Arg Phe Gly Ala Leu Leu Val Asn Pro Gly Gly
            100                 105                 110

ccc ggg gcg tcg gcg gtc gac atg gtc gcc gct atg gca ccc gcg atc      384
Pro Gly Ala Ser Ala Val Asp Met Val Ala Ala Met Ala Pro Ala Ile
        115                 120                 125

gcc gac acc gac att ctc cgc cac ttc gac ctg gtg ggc ttc gac ccg      432
Ala Asp Thr Asp Ile Leu Arg His Phe Asp Leu Val Gly Phe Asp Pro
    130                 135                 140

aga ggg gtc ggc cac tcg acc cct gcg ttg cgg tgt cgc acc gac gcc      480
Arg Gly Val Gly His Ser Thr Pro Ala Leu Arg Cys Arg Thr Asp Ala
145                 150                 155                 160

gag ttc gac gcg tac cgg cgc gat ccg atg gcc gac tac agt ccg gcc      528
Glu Phe Asp Ala Tyr Arg Arg Asp Pro Met Ala Asp Tyr Ser Pro Ala
                165                 170                 175

ggc gtc acc cac gtc gaa cag gtc tac cgg cag ttg gcc cag gac tgt      576
Gly Val Thr His Val Glu Gln Val Tyr Arg Gln Leu Ala Gln Asp Cys
            180                 185                 190

gtt gac cgg atg ggc ttc agc ttc ttg gcc aat atc ggt acc gcg tcc      624
Val Asp Arg Met Gly Phe Ser Phe Leu Ala Asn Ile Gly Thr Ala Ser
```

-continued

```
        195                 200                 205

gtc gca cgg gac atg gac atg gtt cgc caa gcg tta ggt gac gat cag      672
Val Ala Arg Asp Met Asp Met Val Arg Gln Ala Leu Gly Asp Asp Gln
    210                 215                 220

atc aac tac ctc gga tac agc tac ggc acc aag ttg ggc acc gct tac      720
Ile Asn Tyr Leu Gly Tyr Ser Tyr Gly Thr Lys Leu Gly Thr Ala Tyr
225                 230                 235                 240

ctg gaa cgg ttc ggt act cat gtg cgg gcg atg gtc ctc gac ggc gct      768
Leu Glu Arg Phe Gly Thr His Val Arg Ala Met Val Leu Asp Gly Ala
                245                 250                 255

atc gat cca gcc gtt agc cca atc gag gaa agc atc agc caa atg gcg      816
Ile Asp Pro Ala Val Ser Pro Ile Glu Glu Ser Ile Ser Gln Met Ala
            260                 265                 270

gga ttt cag acc gct ttc aat gac tac gcc gcc gac tgc gcc cgc tcg      864
Gly Phe Gln Thr Ala Phe Asn Asp Tyr Ala Ala Asp Cys Ala Arg Ser
        275                 280                 285

ccg gcc tgc cct ctg ggc acc gac tcg gcc cag tgg gtc aac cgc tac      912
Pro Ala Cys Pro Leu Gly Thr Asp Ser Ala Gln Trp Val Asn Arg Tyr
    290                 295                 300

cac gcc ctg gtt gac ccg ctg gtg cag aag ccg ggt aag acg tcg gat      960
His Ala Leu Val Asp Pro Leu Val Gln Lys Pro Gly Lys Thr Ser Asp
305                 310                 315                 320

cca cgt ggc ctg agc tac gcc gac gcg acg acg ggc acc atc aac gcg     1008
Pro Arg Gly Leu Ser Tyr Ala Asp Ala Thr Thr Gly Thr Ile Asn Ala
                325                 330                 335

ctg tac agc cct cag cgc tgg aag tac ctg acc agt ggt ctg ctg ggg     1056
Leu Tyr Ser Pro Gln Arg Trp Lys Tyr Leu Thr Ser Gly Leu Leu Gly
            340                 345                 350

ctg cag cgc ggc agc gac gcc ggc gac ttg ctg gtg ctt gcc gac gac     1104
Leu Gln Arg Gly Ser Asp Ala Gly Asp Leu Leu Val Leu Ala Asp Asp
        355                 360                 365

tat gac ggc cgg gat gca gac ggg cac tac agc aac gac cag gac gcg     1152
Tyr Asp Gly Arg Asp Ala Asp Gly His Tyr Ser Asn Asp Gln Asp Ala
    370                 375                 380

ttc aac gcg gtc cgg tgc gtc tat gcg ccc aca ccg gcc gat cca gcg     1200
Phe Asn Ala Val Arg Cys Val Tyr Ala Pro Thr Pro Ala Asp Pro Ala
385                 390                 395                 400

gcc tgg gtg gcc gcc gac caa cgg atc cgt cag gtc gcc ccg ttc ctt     1248
Ala Trp Val Ala Ala Asp Gln Arg Ile Arg Gln Val Ala Pro Phe Leu
                405                 410                 415

agc tac ggg cag ttc acc gga tcc gcc ccc cgc gat ctg tgc gcg ctg     1296
Ser Tyr Gly Gln Phe Thr Gly Ser Ala Pro Arg Asp Leu Cys Ala Leu
            420                 425                 430

tgg ccg gtg ccg gca acg tcg acg ccg cac ccc gcg gcg ccg gcc ggg     1344
Trp Pro Val Pro Ala Thr Ser Thr Pro His Pro Ala Ala Pro Ala Gly
        435                 440                 445

gct ggc aag gtc gtc gtg gtg tcc acc acc cac gac ccg gcc act ccg     1392
Ala Gly Lys Val Val Val Val Ser Thr Thr His Asp Pro Ala Thr Pro
    450                 455                 460

tat cag tcc ggg gta gac ctg gcc cgc cag ctg ggc gca ccg ctg atc     1440
Tyr Gln Ser Gly Val Asp Leu Ala Arg Gln Leu Gly Ala Pro Leu Ile
465                 470                 475                 480

acc ttc gac ggc acc caa cac act gcg gtg ttc gat ggc aac cag tgt     1488
Thr Phe Asp Gly Thr Gln His Thr Ala Val Phe Asp Gly Asn Gln Cys
                485                 490                 495

gtg gac tct gcg gtg atg cac tat ttt ctc gac ggg acc ttg ccg ccg     1536
Val Asp Ser Ala Val Met His Tyr Phe Leu Asp Gly Thr Leu Pro Pro
            500                 505                 510

acg agt ctg cgg tgc gcg ccc tga                                     1560
```

-continued

```
Thr Ser Leu Arg Cys Ala Pro
        515                 520


<210> SEQ ID NO 4
<211> LENGTH: 519
<212> TYPE: PRT
<213> ORGANISM: Mycobacterium tuberculosis

<400> SEQUENCE: 4

Ala Ala Met Trp Arg Arg Arg Pro Leu Ser Ser Ala Leu Leu Ser Phe
  1               5                  10                  15

Gly Leu Leu Leu Gly Gly Leu Leu Leu Ala Ala Pro Pro Leu Ala Gly
             20                  25                  30

Ala Thr Glu Glu Pro Gly Ala Gly Gln Thr Pro Gly Ala Pro Val Val
         35                  40                  45

Ala Pro Gln Gln Ser Trp Asn Ser Cys Arg Glu Phe Ile Ala Asp Thr
     50                  55                  60

Ser Glu Ile Arg Thr Ala Arg Cys Ala Thr Val Ser Val Pro Val Asp
 65                  70                  75                  80

Tyr Asp Gln Pro Gly Gly Thr Gln Ala Lys Leu Ala Val Ile Arg Val
                 85                  90                  95

Pro Ala Thr Gly Gln Arg Phe Gly Ala Leu Leu Val Asn Pro Gly Gly
            100                 105                 110

Pro Gly Ala Ser Ala Val Asp Met Val Ala Ala Met Ala Pro Ala Ile
        115                 120                 125

Ala Asp Thr Asp Ile Leu Arg His Phe Asp Leu Val Gly Phe Asp Pro
    130                 135                 140

Arg Gly Val Gly His Ser Thr Pro Ala Leu Arg Cys Arg Thr Asp Ala
145                 150                 155                 160

Glu Phe Asp Ala Tyr Arg Arg Asp Pro Met Ala Asp Tyr Ser Pro Ala
                165                 170                 175

Gly Val Thr His Val Glu Gln Val Tyr Arg Gln Leu Ala Gln Asp Cys
            180                 185                 190

Val Asp Arg Met Gly Phe Ser Phe Leu Ala Asn Ile Gly Thr Ala Ser
        195                 200                 205

Val Ala Arg Asp Met Asp Met Val Arg Gln Ala Leu Gly Asp Asp Gln
    210                 215                 220

Ile Asn Tyr Leu Gly Tyr Ser Tyr Gly Thr Lys Leu Gly Thr Ala Tyr
225                 230                 235                 240

Leu Glu Arg Phe Gly Thr His Val Arg Ala Met Val Leu Asp Gly Ala
                245                 250                 255

Ile Asp Pro Ala Val Ser Pro Ile Glu Glu Ser Ile Ser Gln Met Ala
            260                 265                 270

Gly Phe Gln Thr Ala Phe Asn Asp Tyr Ala Ala Asp Cys Ala Arg Ser
        275                 280                 285

Pro Ala Cys Pro Leu Gly Thr Asp Ser Ala Gln Trp Val Asn Arg Tyr
    290                 295                 300

His Ala Leu Val Asp Pro Leu Val Gln Lys Pro Gly Lys Thr Ser Asp
305                 310                 315                 320

Pro Arg Gly Leu Ser Tyr Ala Asp Ala Thr Thr Gly Thr Ile Asn Ala
                325                 330                 335

Leu Tyr Ser Pro Gln Arg Trp Lys Tyr Leu Thr Ser Gly Leu Leu Gly
            340                 345                 350

Leu Gln Arg Gly Ser Asp Ala Gly Asp Leu Leu Val Leu Ala Asp Asp
        355                 360                 365
```

-continued

```
Tyr Asp Gly Arg Asp Ala Asp Gly His Tyr Ser Asn Asp Gln Asp Ala
    370                 375                 380

Phe Asn Ala Val Arg Cys Val Tyr Ala Pro Thr Pro Ala Asp Pro Ala
385                 390                 395                 400

Ala Trp Val Ala Ala Asp Gln Arg Ile Arg Gln Val Ala Pro Phe Leu
                405                 410                 415

Ser Tyr Gly Gln Phe Thr Gly Ser Ala Pro Arg Asp Leu Cys Ala Leu
            420                 425                 430

Trp Pro Val Pro Ala Thr Ser Thr Pro His Pro Ala Ala Pro Ala Gly
        435                 440                 445

Ala Gly Lys Val Val Val Val Ser Thr Thr His Asp Pro Ala Thr Pro
    450                 455                 460

Tyr Gln Ser Gly Val Asp Leu Ala Arg Gln Leu Gly Ala Pro Leu Ile
465                 470                 475                 480

Thr Phe Asp Gly Thr Gln His Thr Ala Val Phe Asp Gly Asn Gln Cys
                485                 490                 495

Val Asp Ser Ala Val Met His Tyr Phe Leu Asp Gly Thr Leu Pro Pro
            500                 505                 510

Thr Ser Leu Arg Cys Ala Pro
        515


<210> SEQ ID NO 5
<211> LENGTH: 903
<212> TYPE: DNA
<213> ORGANISM: Mycobacterium tuberculosis
<220> FEATURE:
<221> NAME/KEY: CDS
<222> LOCATION: (1)..(903)
<220> FEATURE:
<221> NAME/KEY: mat_peptide
<222> LOCATION: (1)..(903)

<400> SEQUENCE: 5

gat tac gaa cag gac tgg gac ggc gtt gcg ata acc ctg acg cgg tcg       48
Asp Tyr Glu Gln Asp Trp Asp Gly Val Ala Ile Thr Leu Thr Arg Ser
  1               5                  10                  15

cag ctg tat cgg cga acg ctg aat gtg gca cag gag ctg agc cgt tgt       96
Gln Leu Tyr Arg Arg Thr Leu Asn Val Ala Gln Glu Leu Ser Arg Cys
             20                  25                  30

ggt tcc acg ggt gac cgc gtg gtg atc tct gct ccg cag gga ctc gag      144
Gly Ser Thr Gly Asp Arg Val Val Ile Ser Ala Pro Gln Gly Leu Glu
         35                  40                  45

tac gtc gtc gcc tat ctc ggc gcg ttg cag gcc ggg cgc atc gcc gtg      192
Tyr Val Val Ala Tyr Leu Gly Ala Leu Gln Ala Gly Arg Ile Ala Val
     50                  55                  60

ccg ctt tcg gtt cca caa ggc ggc gtt acc gat gaa cgt tcc gat tcg      240
Pro Leu Ser Val Pro Gln Gly Gly Val Thr Asp Glu Arg Ser Asp Ser
 65                  70                  75                  80

gta ctg agt gat tcg tcg ccg gtg gcc att ctc act aca tcg tct gcc      288
Val Leu Ser Asp Ser Ser Pro Val Ala Ile Leu Thr Thr Ser Ser Ala
                 85                  90                  95

gtg gac gac gtc gtg caa cat gtt gcg cgg cgg ccc ggg gaa tcc ccg      336
Val Asp Asp Val Val Gln His Val Ala Arg Arg Pro Gly Glu Ser Pro
            100                 105                 110

cca tca att atc gaa gtt gat ttg ctc gat ctg gac gct ccg aat ggg      384
Pro Ser Ile Ile Glu Val Asp Leu Leu Asp Leu Asp Ala Pro Asn Gly
        115                 120                 125

tat acc ttc aaa gaa gac gag tat cca tct acc gcg tat ttg caa tac      432
Tyr Thr Phe Lys Glu Asp Glu Tyr Pro Ser Thr Ala Tyr Leu Gln Tyr
```

-continued

```
    130                 135                 140

acc tcc ggg tcc acc cgc acg ccc gct ggc gtg gtg atg tcc cat cag      480
Thr Ser Gly Ser Thr Arg Thr Pro Ala Gly Val Val Met Ser His Gln
145                 150                 155                 160

aac gtt cgg gtt aat ttc gaa cag ctg atg tct ggc tac ttt gcg gat      528
Asn Val Arg Val Asn Phe Glu Gln Leu Met Ser Gly Tyr Phe Ala Asp
                165                 170                 175

acc gac ggg att cca ccg cca aat tcc gca ctc gta tcc tgg cta ccc      576
Thr Asp Gly Ile Pro Pro Pro Asn Ser Ala Leu Val Ser Trp Leu Pro
            180                 185                 190

ttc tac cac gac atg ggt ttg gta ata gga att tgc gca cca att ctg      624
Phe Tyr His Asp Met Gly Leu Val Ile Gly Ile Cys Ala Pro Ile Leu
        195                 200                 205

ggt gga tac ccc gcg gtg ctc acc agc ccg gtg tcg ttc ctg cag cgc      672
Gly Gly Tyr Pro Ala Val Leu Thr Ser Pro Val Ser Phe Leu Gln Arg
    210                 215                 220

ccg gcc cgg tgg atg cac ttg atg gcc agc gat ttt cac gcc ttt tcg      720
Pro Ala Arg Trp Met His Leu Met Ala Ser Asp Phe His Ala Phe Ser
225                 230                 235                 240

gca gca ccg aat ttc gcc ttt gaa cta gcg gca cga aga aca acc gac      768
Ala Ala Pro Asn Phe Ala Phe Glu Leu Ala Ala Arg Arg Thr Thr Asp
                245                 250                 255

gac gac atg gcc ggg cgt gac ctc ggc aac ata ctg acc atc ctc agc      816
Asp Asp Met Ala Gly Arg Asp Leu Gly Asn Ile Leu Thr Ile Leu Ser
            260                 265                 270

ggt agc gag cgg gta cag gcc gcg acg atc aag cgc ttc gcc gac cgc      864
Gly Ser Glu Arg Val Gln Ala Ala Thr Ile Lys Arg Phe Ala Asp Arg
        275                 280                 285

ttt gct cgc ttc aat ctg cag gag agg gtg aaa gct taa                  903
Phe Ala Arg Phe Asn Leu Gln Glu Arg Val Lys Ala
    290                 295                 300


<210> SEQ ID NO 6
<211> LENGTH: 300
<212> TYPE: PRT
<213> ORGANISM: Mycobacterium tuberculosis

<400> SEQUENCE: 6

Asp Tyr Glu Gln Asp Trp Asp Gly Val Ala Ile Thr Leu Thr Arg Ser
  1               5                  10                  15

Gln Leu Tyr Arg Arg Thr Leu Asn Val Ala Gln Glu Leu Ser Arg Cys
            20                  25                  30

Gly Ser Thr Gly Asp Arg Val Val Ile Ser Ala Pro Gln Gly Leu Glu
        35                  40                  45

Tyr Val Val Ala Tyr Leu Gly Ala Leu Gln Ala Gly Arg Ile Ala Val
     50                  55                  60

Pro Leu Ser Val Pro Gln Gly Gly Val Thr Asp Glu Arg Ser Asp Ser
 65                  70                  75                  80

Val Leu Ser Asp Ser Ser Pro Val Ala Ile Leu Thr Thr Ser Ser Ala
                 85                  90                  95

Val Asp Asp Val Val Gln His Val Ala Arg Arg Pro Gly Glu Ser Pro
            100                 105                 110

Pro Ser Ile Ile Glu Val Asp Leu Leu Asp Leu Asp Ala Pro Asn Gly
        115                 120                 125

Tyr Thr Phe Lys Glu Asp Glu Tyr Pro Ser Thr Ala Tyr Leu Gln Tyr
    130                 135                 140

Thr Ser Gly Ser Thr Arg Thr Pro Ala Gly Val Val Met Ser His Gln
145                 150                 155                 160
```

-continued

```
Asn Val Arg Val Asn Phe Glu Gln Leu Met Ser Gly Tyr Phe Ala Asp
                165                 170                 175

Thr Asp Gly Ile Pro Pro Pro Asn Ser Ala Leu Val Ser Trp Leu Pro
            180                 185                 190

Phe Tyr His Asp Met Gly Leu Val Ile Gly Ile Cys Ala Pro Ile Leu
        195                 200                 205

Gly Gly Tyr Pro Ala Val Leu Thr Ser Pro Val Ser Phe Leu Gln Arg
    210                 215                 220

Pro Ala Arg Trp Met His Leu Met Ala Ser Asp Phe His Ala Phe Ser
225                 230                 235                 240

Ala Ala Pro Asn Phe Ala Phe Glu Leu Ala Ala Arg Arg Thr Thr Asp
                245                 250                 255

Asp Asp Met Ala Gly Arg Asp Leu Gly Asn Ile Leu Thr Ile Leu Ser
            260                 265                 270

Gly Ser Glu Arg Val Gln Ala Ala Thr Ile Lys Arg Phe Ala Asp Arg
        275                 280                 285

Phe Ala Arg Phe Asn Leu Gln Glu Arg Val Lys Ala
    290                 295                 300


<210> SEQ ID NO 7
<211> LENGTH: 432
<212> TYPE: DNA
<213> ORGANISM: Mycobacterium tuberculosis
<220> FEATURE:
<221> NAME/KEY: CDS
<222> LOCATION: (1)..(432)
<220> FEATURE:
<221> NAME/KEY: mat_peptide
<222> LOCATION: (1)..(432)

<400> SEQUENCE: 7

gcc acc acc ctt ccc gtt cag cgc cac ccg cgg tcc ctc ttc ccc gag       48
Ala Thr Thr Leu Pro Val Gln Arg His Pro Arg Ser Leu Phe Pro Glu
  1               5                  10                  15

ttt tct gag ctg ttc gcg gcc ttc ccg tca ttc gcc gga ctc cgg ccc       96
Phe Ser Glu Leu Phe Ala Ala Phe Pro Ser Phe Ala Gly Leu Arg Pro
             20                  25                  30

acc ttc gac acc cgg ttg atg cgg ctg gaa gac gag atg aaa gag ggg      144
Thr Phe Asp Thr Arg Leu Met Arg Leu Glu Asp Glu Met Lys Glu Gly
         35                  40                  45

cgc tac gag gta cgc gcg gag ctt ccc ggg gtc gac ccc gac aag gac      192
Arg Tyr Glu Val Arg Ala Glu Leu Pro Gly Val Asp Pro Asp Lys Asp
     50                  55                  60

gtc cac att atg gtc cgc gat ggt cag ctg acc atc aag gcc gag cgc      240
Val His Ile Met Val Arg Asp Gly Gln Leu Thr Ile Lys Ala Glu Arg
 65                  70                  75                  80

acc gag cag aag gac tta gac ggt cgc tcg gaa ttc gcg tac ggt tcc      288
Thr Glu Gln Lys Asp Leu Asp Gly Arg Ser Glu Phe Ala Tyr Gly Ser
                 85                  90                  95

ttc gtt cgc acg gtg tcg ctg ccg gta ggt gct gac gag gac gac att      336
Phe Val Arg Thr Val Ser Leu Pro Val Gly Ala Asp Glu Asp Asp Ile
            100                 105                 110

aag gcc acc tac gac aag ggc att ctt act gtg tcg gtg gcg gtt tcg      384
Lys Ala Thr Tyr Asp Lys Gly Ile Leu Thr Val Ser Val Ala Val Ser
        115                 120                 125

gaa ggg aag cca acc gaa aag cac att cag atc cgg tcc acc aac tga      432
Glu Gly Lys Pro Thr Glu Lys His Ile Gln Ile Arg Ser Thr Asn
    130                 135                 140
```

-continued

```
<210> SEQ ID NO 8
<211> LENGTH: 143
<212> TYPE: PRT
<213> ORGANISM: Mycobacterium tuberculosis

<400> SEQUENCE: 8

Ala Thr Thr Leu Pro Val Gln Arg His Pro Arg Ser Leu Phe Pro Glu
  1               5                  10                  15

Phe Ser Glu Leu Phe Ala Ala Phe Pro Ser Phe Ala Gly Leu Arg Pro
             20                  25                  30

Thr Phe Asp Thr Arg Leu Met Arg Leu Glu Asp Glu Met Lys Glu Gly
         35                  40                  45

Arg Tyr Glu Val Arg Ala Glu Leu Pro Gly Val Asp Pro Asp Lys Asp
     50                  55                  60

Val His Ile Met Val Arg Asp Gly Gln Leu Thr Ile Lys Ala Glu Arg
 65                  70                  75                  80

Thr Glu Gln Lys Asp Leu Asp Gly Arg Ser Glu Phe Ala Tyr Gly Ser
                 85                  90                  95

Phe Val Arg Thr Val Ser Leu Pro Val Gly Ala Asp Glu Asp Asp Ile
            100                 105                 110

Lys Ala Thr Tyr Asp Lys Gly Ile Leu Thr Val Ser Val Ala Val Ser
        115                 120                 125

Glu Gly Lys Pro Thr Glu Lys His Ile Gln Ile Arg Ser Thr Asn
    130                 135                 140


<210> SEQ ID NO 9
<211> LENGTH: 1161
<212> TYPE: DNA
<213> ORGANISM: Mycobacterium tuberculosis
<220> FEATURE:
<221> NAME/KEY: CDS
<222> LOCATION: (1)..(1161)
<220> FEATURE:
<221> NAME/KEY: mat_peptide
<222> LOCATION: (1)..(1161)

<400> SEQUENCE: 9

aat tcg atg cca gtc ccg ccg gcg cca cca gcg ccg ccg tca ccg atc       48
Asn Ser Met Pro Val Pro Pro Ala Pro Pro Ala Pro Pro Ser Pro Ile
  1               5                  10                  15

aac ccg ccg gtg ccg ccg gtg ccg ccg cta ccg gcc gcg ccc cgg acg       96
Asn Pro Pro Val Pro Pro Val Pro Pro Leu Pro Ala Ala Pro Arg Thr
             20                  25                  30

ctg tcg ccg ccg gta ccg ccg gcg ccg ccg tcg ccg atc agc ttg gcg      144
Leu Ser Pro Pro Val Pro Pro Ala Pro Pro Ser Pro Ile Ser Leu Ala
         35                  40                  45

gcc ccg ccg ctg cca ccg gac ccg ccg atg ccg ccg gcc att tgg tcc      192
Ala Pro Pro Leu Pro Pro Asp Pro Pro Met Pro Pro Ala Ile Trp Ser
     50                  55                  60

gca ctg gag gcg ccg aac cct ccg gtg ccc ccg gcg ccg ccg gga ccg      240
Ala Leu Glu Ala Pro Asn Pro Pro Val Pro Pro Ala Pro Pro Gly Pro
 65                  70                  75                  80

aac agt gcg ccg gca ccg ccg atg ccg ccg acg cct cct ttg ccg ccg      288
Asn Ser Ala Pro Ala Pro Pro Met Pro Pro Thr Pro Pro Leu Pro Pro
                 85                  90                  95

gtg ccg ccg ggg tcg ggc gcg ccg aga ccg gtt ccg gcg gtg ccg cca      336
Val Pro Pro Gly Ser Gly Ala Pro Arg Pro Val Pro Ala Val Pro Pro
            100                 105                 110

atg ccg cca gcg ccg aag agg atg ccg gcg ttg ccg ccc gcc ccg ccg      384
Met Pro Pro Ala Pro Lys Arg Met Pro Ala Leu Pro Pro Ala Pro Pro
        115                 120                 125
```

-continued

```
gcc ccg ccc tca ccg ccc acg agt tgg tta gcg gtg cca gtt ccg ccg      432
Ala Pro Pro Ser Pro Pro Thr Ser Trp Leu Ala Val Pro Val Pro Pro
    130                 135                 140

gtg ccg ccg gtc ccg ccg ttg ccg gtg aag atg ccg ccg tcg cct ccg      480
Val Pro Pro Val Pro Pro Leu Pro Val Lys Met Pro Pro Ser Pro Pro
145                 150                 155                 160

gtg ccg ccg ttc cct ccg gcc gag ccg gag act ccg aac ccg ccg gcg      528
Val Pro Pro Phe Pro Pro Ala Glu Pro Glu Thr Pro Asn Pro Pro Ala
                165                 170                 175

ccg ccg gca ccg cca ttg gag aac agc ccg ccg ccc ccg ccg gtg ccg      576
Pro Pro Ala Pro Pro Leu Glu Asn Ser Pro Pro Pro Pro Pro Val Pro
            180                 185                 190

ccg gtg cca ccg gtg ccc ccg ttg acg ctc aac ccg ccg gtg ccg ccg      624
Pro Val Pro Pro Val Pro Pro Leu Thr Leu Asn Pro Pro Val Pro Pro
        195                 200                 205

gca ccg ccg gcg gcc aac acc tcg aac agc ccg ctg cga ccg ccg gcc      672
Ala Pro Pro Ala Ala Asn Thr Ser Asn Ser Pro Leu Arg Pro Pro Ala
    210                 215                 220

ccg ccg gcg cca ccg ttg aag cct ggc ccg ccg gcc ccg ccg atg cca      720
Pro Pro Ala Pro Pro Leu Lys Pro Gly Pro Pro Ala Pro Pro Met Pro
225                 230                 235                 240

ccg gct ccg aac agc ccg gcc gcc ccg ccg tcg ccg ccg agc ccg cct      768
Pro Ala Pro Asn Ser Pro Ala Ala Pro Pro Ser Pro Pro Ser Pro Pro
                245                 250                 255

gtg ccg gtg ttc ccg act ccg ccg ggc ccc ccg gcg ccg ccg gag ccg      816
Val Pro Val Phe Pro Thr Pro Pro Gly Pro Pro Ala Pro Pro Glu Pro
            260                 265                 270

aac agc agc ccg ccg gcc ccg ccg gcc ccg cca gcc gcg ccg ttg ccc      864
Asn Ser Ser Pro Pro Ala Pro Pro Ala Pro Pro Ala Ala Pro Leu Pro
        275                 280                 285

ggg ccg tca ccc ccg gcc cca ccc gcc ccg ccg ttg ccg aat agc ccc      912
Gly Pro Ser Pro Pro Ala Pro Pro Ala Pro Pro Leu Pro Asn Ser Pro
    290                 295                 300

gcg gct cca cct ggg ccg ccg gcc tgg ccg ggc gcc ccg gac ccg ccg      960
Ala Ala Pro Pro Gly Pro Pro Ala Trp Pro Gly Ala Pro Asp Pro Pro
305                 310                 315                 320

gcc ccg ccg ttg ccg tac agc agc ccg ccg gcc ccg ccg gct tgc ccg     1008
Ala Pro Pro Leu Pro Tyr Ser Ser Pro Pro Ala Pro Pro Ala Cys Pro
                325                 330                 335

gtc ccc ggt gcg ccg ttg gcg ccg ttg ccg atc agc gga cgc ccc agc     1056
Val Pro Gly Ala Pro Leu Ala Pro Leu Pro Ile Ser Gly Arg Pro Ser
            340                 345                 350

aac agc tgg gtg ggc gtg ttc aca atg ttg agc agg ccc tcc aac ggc     1104
Asn Ser Trp Val Gly Val Phe Thr Met Leu Ser Arg Pro Ser Asn Gly
        355                 360                 365

gcc gcg gcg gcg gcc tca gcg ctc gcg tac gcg cca gcg ccc gca gta     1152
Ala Ala Ala Ala Ala Ser Ala Leu Ala Tyr Ala Pro Ala Pro Ala Val
    370                 375                 380

aag gtt tga                                                         1161
Lys Val
385
```

```
<210> SEQ ID NO 10
<211> LENGTH: 386
<212> TYPE: PRT
<213> ORGANISM: Mycobacterium tuberculosis

<400> SEQUENCE: 10

Asn Ser Met Pro Val Pro Pro Ala Pro Pro Ala Pro Pro Ser Pro Ile
  1               5                  10                  15
```

-continued

```
Asn Pro Pro Val Pro Pro Val Pro Pro Leu Pro Ala Ala Pro Arg Thr
            20                  25                  30

Leu Ser Pro Pro Val Pro Pro Ala Pro Pro Ser Pro Ile Ser Leu Ala
        35                  40                  45

Ala Pro Pro Leu Pro Pro Asp Pro Pro Met Pro Pro Ala Ile Trp Ser
    50                  55                  60

Ala Leu Glu Ala Pro Asn Pro Pro Val Pro Pro Ala Pro Pro Gly Pro
65                  70                  75                  80

Asn Ser Ala Pro Ala Pro Pro Met Pro Pro Thr Pro Pro Leu Pro Pro
                85                  90                  95

Val Pro Pro Gly Ser Gly Ala Pro Arg Pro Val Pro Ala Val Pro Pro
            100                 105                 110

Met Pro Pro Ala Pro Lys Arg Met Pro Ala Leu Pro Pro Ala Pro Pro
        115                 120                 125

Ala Pro Pro Ser Pro Pro Thr Ser Trp Leu Ala Val Pro Val Pro Pro
    130                 135                 140

Val Pro Pro Val Pro Pro Leu Pro Val Lys Met Pro Pro Ser Pro Pro
145                 150                 155                 160

Val Pro Pro Phe Pro Pro Ala Glu Pro Glu Thr Pro Asn Pro Pro Ala
                165                 170                 175

Pro Pro Ala Pro Pro Leu Glu Asn Ser Pro Pro Pro Pro Pro Val Pro
            180                 185                 190

Pro Val Pro Pro Val Pro Pro Leu Thr Leu Asn Pro Pro Val Pro Pro
        195                 200                 205

Ala Pro Pro Ala Ala Asn Thr Ser Asn Ser Pro Leu Arg Pro Pro Ala
    210                 215                 220

Pro Pro Ala Pro Pro Leu Lys Pro Gly Pro Pro Ala Pro Pro Met Pro
225                 230                 235                 240

Pro Ala Pro Asn Ser Pro Ala Ala Pro Pro Ser Pro Pro Ser Pro Pro
                245                 250                 255

Val Pro Val Phe Pro Thr Pro Pro Gly Pro Pro Ala Pro Pro Glu Pro
            260                 265                 270

Asn Ser Ser Pro Pro Ala Pro Pro Ala Pro Pro Ala Ala Pro Leu Pro
        275                 280                 285

Gly Pro Ser Pro Pro Ala Pro Pro Ala Pro Pro Leu Pro Asn Ser Pro
    290                 295                 300

Ala Ala Pro Pro Gly Pro Pro Ala Trp Pro Gly Ala Pro Asp Pro Pro
305                 310                 315                 320

Ala Pro Pro Leu Pro Tyr Ser Ser Pro Pro Ala Pro Pro Ala Cys Pro
                325                 330                 335

Val Pro Gly Ala Pro Leu Ala Pro Leu Pro Ile Ser Gly Arg Pro Ser
            340                 345                 350

Asn Ser Trp Val Gly Val Phe Thr Met Leu Ser Arg Pro Ser Asn Gly
        355                 360                 365

Ala Ala Ala Ala Ala Ser Ala Leu Ala Tyr Ala Pro Ala Pro Ala Val
    370                 375                 380

Lys Val
385
```

<210> SEQ ID NO 11
<211> LENGTH: 15
<212> TYPE: PRT
<213> ORGANISM: Mycobacterium tuberculosis -continued

<400> SEQUENCE: 11

Ser Lys Leu Ile Glu Tyr Asp Glu Leu Ala Leu Glu Ala Met Glu
1 5 10 15

<210> SEQ ID NO 12
<211> LENGTH: 15
<212> TYPE: PRT
<213> ORGANISM: Mycobacterium tuberculosis

<400> SEQUENCE: 12

Ser Lys Leu Ile Glu Tyr Asp Glu Thr Ala Arg His Ala Met Glu
1 5 10 15

<210> SEQ ID NO 13
<211> LENGTH: 12
<212> TYPE: PRT
<213> ORGANISM: Mycobacterium tuberculosis

<400> SEQUENCE: 13

Ala Lys Thr Ile Ala Tyr Asp Glu Glu Ala Arg Val
1 5 10

<210> SEQ ID NO 14
<211> LENGTH: 10
<212> TYPE: PRT
<213> ORGANISM: Mycobacterium tuberculosis

<400> SEQUENCE: 14

Ala Lys Thr Ile Ala Tyr Asp Glu Glu Ala
1 5 10

<210> SEQ ID NO 15
<211> LENGTH: 14
<212> TYPE: PRT
<213> ORGANISM: Mycobacterium tuberculosis

<400> SEQUENCE: 15

Ala Glu Val Asp Ala Tyr Lys Phe Asp Pro Asp Ala Val Asp
1 5 10

<210> SEQ ID NO 16
<211> LENGTH: 12
<212> TYPE: PRT
<213> ORGANISM: Mycobacterium tuberculosis

<400> SEQUENCE: 16

Ala Glu Phe Asp Ala Tyr Arg Arg Asp Pro Met Ala
1 5 10

<210> SEQ ID NO 17
<211> LENGTH: 13
<212> TYPE: PRT
<213> ORGANISM: Mycobacterium tuberculosis

<400> SEQUENCE: 17

Ala Glu Tyr Thr Leu Pro Asp Leu Asp Trp Asp Tyr Gly
1 5 10

<210> SEQ ID NO 18
<211> LENGTH: 13
<212> TYPE: PRT
<213> ORGANISM: Mycobacterium tuberculosis

<400> SEQUENCE: 18

-continued

```
Ala Glu Tyr Thr Leu Pro Asp Leu Asp Trp Asp Tyr Gly
  1               5                  10


<210> SEQ ID NO 19
<211> LENGTH: 11
<212> TYPE: PRT
<213> ORGANISM: Mycobacterium tuberculosis

<400> SEQUENCE: 19

Met Glu Ile Asp Ile Leu Ala Val Ala Ala Pro
  1               5                  10


<210> SEQ ID NO 20
<211> LENGTH: 11
<212> TYPE: PRT
<213> ORGANISM: Mycobacterium tuberculosis

<400> SEQUENCE: 20

Ile Glu Val Asp Leu Leu Asp Leu Asp Ala Pro
  1               5                  10


<210> SEQ ID NO 21
<211> LENGTH: 13
<212> TYPE: PRT
<213> ORGANISM: Mycobacterium tuberculosis

<400> SEQUENCE: 21

Ala Thr Thr Leu Pro Val Gln Arg His Asp Ala Arg Leu
  1               5                  10


<210> SEQ ID NO 22
<211> LENGTH: 12
<212> TYPE: PRT
<213> ORGANISM: Mycobacterium tuberculosis

<400> SEQUENCE: 22

Ala Thr Leu Pro Val Gln Arg His Pro Arg Ser Leu
  1               5                  10
```

BACTERIAL-DERIVED MOLECULES AND THERAPEUTIC AND DIAGNOSTIC USES THEREFOR

This application claims priority on provisional Application No. 60/112,499 filed on Dec. 16, 1998, the entire contents of which are hereby incorporated by reference.

FIELD OF THE INVENTION

The present invention relates generally to molecules derived from a *Mycobacterium* species and recombinant, synthetic, derivative, homologue and analogue forms of said molecules. The molecules of the present invention are useful in diagnostic assays for *Mycobacterium* in biological and environmental samples. The present invention is particularly directed to molecules derived from *Mycobacterium tuberculosis* and related organisms and even more particularly to recombinant forms of these molecules or synthetic, derivative, homologue or analogue forms thereof and their use in diagnostic and therapeutic protocols for tuberculosis or other disease conditions associated with *M. tuberculosis* or related organisms.

BACKGROUND OF THE INVENTION

Bibliographic details of the publications numerically referred to in this specification are collected at the end of the description.

Bacterial infection represents a major cause of mortality and morbidity in human and other animal populations. One important group of bacteria are the mycobacteria. The mycobacteria are defined on the basis of a distinctive staining property conferred by their lipid-rich cell walls. The mycobacteria are relatively impermeable to various basic dyes but once stained, they retain dyes with tenacity. The mycobacteria have been referred to as "acid-fast" bacteria since they resist decolorization with acidified organic solvents (1). Mycobacteria range from widespread innocuous inhabitants of soil and water to organisms responsible for devastating and chronic diseases notably in tuberculosis and leprosy caused by *Mycobacterium tuberculosis* and *Mycobacterium leprae*, respectively.

Leprosy involves infection in skin tissue and can lead to disfigurement. Tuberculosis is generally confined to internal organs. Although both leprosy and tuberculosis were largely controlled by chemical intervention and improvements in living conditions, tuberculosis is now re-emerging as a major health problem. On an annual basis, reportedly between 2 and 3 million people die from tuberculosis, mostly in developing countries (2).

Conventional diagnostic tests for tuberculosis include chest X-ray, detecting the presence of acid-fast bacilli in clinical specimens and the skin test using tuberculin PPD (Purified Protein Derivative) [3]. However, these procedures are time intensive, frequently the results are ambiguous and X-ray machines are expensive and generally not portable enough for use in developing countries.

Nucleic acid probes can be used in a polymerase chain reaction (PCR) to specifically detect a mycobacterial infection, but require complex equipment, highly skilled staff and are too expensive for the developing countries (4). Rapid serological diagnostic tests are available on an ELISA or "strip" format which uses antigen(s) to detect antibody in sera (5).

However, currently there is no satisfactory test for tuberculosis. A majority of *M. tuberculosis* antigens studied to date have homology with analogues proteins of other microorganisms that may or may not be pathogenic; resulting in cross-reactivity of these antigens to reactive serum antibodies in patients with inactive TB or nontuberculous infections (6). Hence, positive test results produced by these known antigens are generally unreliable and supplementary tests are required to confirm the presence of the tuberculosis infection.

In work leading up to the present invention, the inventors sought to use recombinant molecules from *M. tuberculosis* in the development of a highly specific and sensitive diagnostic test for tuberculosis. The same or similar molecules are also proposed for use as therapeutic agents for the treatment of tuberculosis.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The subject specification contains nucleotide and amino acid sequence information prepared using the programme PatentIn Version 2.1 presented herein after the bibliography. Each nucleotide or amino acid sequence is identified in the sequence listing by the numeric indicator <210>followed by the sequence identifier (e.g. <210>1, <210>2, etc). The length, type of sequence (DNA, protein (PRT), etc) and source organism for each nucleotide or amino acid sequence are indicate by information provided in the numeric indicator fields <211>, <212>and <213>, respectively. Nucleotide and amino acid sequences referred to in the specification are defined by the information provided in numeric indicator field <400>followed by the sequence identifier (eg. <400>1, <400>2, etc).

One aspect of the present invention provides an isolated polypeptide or a derivative, homologue, analogue or functional equivalent thereof wherein said polypeptide is obtainable from a species of *Mycobacterium* and which polypeptide is immunointeractive with sera from a human, animal or avian species exposed to said species of *Mycobacterium* or its relative or antigenic parts thereof but which polypeptide is substantially not immunointeractive with sera from a human, animal or avian species not prior exposed to said species of *Mycobacterium* or its relative or its antigenic parts.

Another aspect of the present invention is directed to an isolated polypeptide or a derivative, homologue, analogue or functional equivalent thereof wherein said polypeptide is obtainable from *M. tuberculosis* or a related organism and which polypeptide is immunointeractive with sera from a human previously exposed to *M. tuberculosis* or an antigenic extract therefrom but is substantially not immunointeractive with human sera not previously exposed to *M. tuberculosis* or a antigenic extract thereof.

Yet another aspect of the present invention relates to an isolated polypeptide obtainable from *M. tuberculosis* or related organism or a derivative, homologue, analogue or chemical equivalent of said polypeptide which polypeptide is immunointeractive with sera from a human patient with active pulmonary or extra-pulmonary tuberculosis but is substantially not immunointeractive with sera from a subject not previously infected with *M. tuberculosis* or sera from a subject who otherwise has no immunological memory for said polypeptide or antigenic derivatives thereof.

Still yet another aspect of the present invention provides a polypeptide having a molecular weight selected from about 5 kDa to about 100 kDa or a derivative, homologue, analogue or functional equivalent thereof said polypeptide obtainable from *M. tuberculosis* and wherein polypeptide is immunointeractive with sera from a patient with active pulmonary or extra-pulmonary tuberculosis but substantially not immunointeractive with sera from a subject who does not have active pulmonary or extra-pulmonary tuberculosis.

In still yet another aspect of the present invention there is provided a polypeptide having a molecular weight selected from about 10 to 20 kDa, 28 to 38 kDa, 38 to 48 kDa, 53 to 63 kDa and 55 to 65 kDa or a derivative, homologue, analogue or functional equivalent thereof said polypeptide obtainable from *M. tuberculosis* and wherein polypeptide is immunointeractive with sera from a patient with active pulmonary or extra-pulmonary tuberculosis but substantially not immunointeractive with sera from a subject who does not have active pulmonary or extra-pulmonary tuberculosis.

Yet a further aspect of the present invention provides a polypeptide comprising an amino acid sequence selected from SEQ ID NO:2, SEQ ID NO:4, SEQ ID NO:6, SEQ ID NO:8, SEQ ID NO:10, or an amino acid sequence having at least 60% similarity to any one of said sequences.

Still yet a further aspect of the present invention provides a polypeptide encoded by a nucleotide sequence selected from SEQ ID NO:1, SEQ ID NO:3, SEQ ID NO:5, SEQ ID NO:7, SEQ ID NO:9, or a nucleotide sequence having at least 60% similarity to any one of said sequences or a nucleotide sequence capable of hybridizing to any one of said sequences under low stringency conditions at 42° C.

Another aspect of the present invention contemplates a method of isolating a polypeptide from *Mycobacterium* species said method comprising culturing cells of said *Mycobacterium* species in a growth medium to increase the number of cells to a sufficient population, harvesting said cells and subjecting said cells to protein extraction techniques to extract protein from said cells, fractionating the extracted protein and subjecting said protein to binding analysis with antibodies to said *Mycobacterium* species or antigenic portions thereof and isolating the polypeptides to which antibodies interact.

Yet another aspect of the present invention is directed to an isolated nucleic acid molecule comprising a sequence of nucleotides encoding or complementary to a sequence encoding a polypeptide obtainable from a species of *Mycobacterium* and which polypeptide is immunointeractive with sera from a human, animal or avian species exposed to said species of *Mycobacterium* or its relative or antigenic parts thereof but which polypeptide is substantially not immunointeractive with sera from a human, animal or avian species not prior exposed to said species of *Mycobacterium* or its relative or its antigenic parts.

Another aspect of the present invention contemplates a method for detecting the presence of *M. tuberculosis* such as in a patient suffering from tuberculosis said method comprising contacting a biological sample from a patient or subject with an antibody specific for a polypeptide from said *M. tuberculosis* and detecting a complex between said polypeptide and said antibody.

Yet another aspect of the present invention provides a method for detecting the presence of *M. tuberculosis* such as in a patient suffering from tuberculosis said method comprising contacting a sera sample from a patient or subject with a polypeptide from *M. tuberculosis* and detecting a complex between said polypeptide and an antibody in said sera.

Still yet another aspect of the present invention provides an assay device for *M. tuberculosis* comprising a solid support having immobilized thereon one or more polypeptides obtainable from *M. tuberculosis* or derivatives, homologues, analogues or antigenic equivalents thereof and a portion of said solid support adapted for receiving a sample from a human subject to be tested wherein said sample would contain an antibody specific for said *M. tuberculosis* polypeptide if said subject has been exposed to *M. tuberculosis* wherein upon contact between the antibody from the subject and the immobilized polypeptide, a complex forms and said complex is detected by an anti-human immunoglobulin labelled with a reporter molecule.

BRIEF DESCRIPTION OF THE FIGURES

FIG. 1 is a diagrammatic representation of the strategy for the isolation and expression of *M. tuberculosis* protein antigens.

FIG. 2 is a photographic representation showing (A) gel purified and concentrated *M. tuberculosis* protein bands (B.1, 2, 3, 4, 5, 6, 8, 9, 10) blotted onto PVDF membrane and were then excised for N-terminal sequencing; (B) concentrated *M. tuberculosis* protein bands were blotted onto nitrocellulose membrane and immuno-screened using pooled normal (N) and active (A) sera, respectively. Positive bands (arrows) were observed with A but not with N.

FIG. 3 is a representation showing the results of homology search against the GenBank protein sequence databases. Proteins showing the highest homology to the *M. tuberculosis* protein bands are as shown.

SEQ ID NO:11 SKLIEYDELALEAME
SEQ ID NO:12 SKLIEYDETARHAME
SEQ ID NO:13 AKTIAYDEEARV
SEQ ID NO:14 AKTIAYDEEA
SEQ ID NO:15 AEVDAYKFDPDAVD
SEQ ID NO:16 AEFDAYRRDPMA
SEQ ID NO:17 AEYTLPDLDWDYG
SEQ ID NO:18 AEYTLPDLDWDYG
SEQ ID NO:19 MEIDILAVAAP
SEQ ID NO:20 IEVDLLDLDAP
SEQ ID NO:21 ATTLPVQRHDARL
SEQ ID NO:22 ATLPVQRHPRSL.

FIG. 4 is a photographical representation of Western blot screening of recombinant *M. tuberculosis* antigens. (A) Arrows indicate the position of the recombinant antigens on the membrane. M=Kaleidoscope protein marker and H=strip probed with anti-RGSHis, C=a positive control of strips probed with known human serum reactive to the specific recombinant antigen. (B) Reactivity is estimated based on the intensity of the band.

FIG. 5 is a representation of the percentage of reactivity of recombinant TB antigens against different sera panels. A known 38 kDa antigen (7, 8) of *M. tuberculosis* was included in the screening. The gene (GeneBank Accession # M30046) for this antigen was cloned, expressed in pQE30 and partially purified. Also shown are the percentages of reactivity of sera samples detected by a commercially available rapid TB diagnostic kit from ICT (Amrad).

FIG. 6 is a graphical representation of a result from a Western screen using sera from normal individuals or patients with extrapulmonary tuberculosis, pulmonary tuberculosis and inactive tuberculosis.

FIG. 7 is a graphical representation showing the percentage of reactivity for various combinations of these recombinant antigens against the inactive, active (pulmonary) and active (extra-pulmonary) sera panels respectively.

FIG. 8 is a graphical representation showing the comparison of reactivity against the different sera panel for the combination of all the recombinant TB antigens compared to the ICT TB diagnostic kit. The graph shows that the percentage of reactivity for the active sera panel (pulmonary and extra-pulmonary) is higher than that observed for the kit.

FIG. 9 is a graphical representation showing that the combination of antigens (B.6+B. 10+MMP+38 kDa) gave a sensitivity (60–70%) higher than that observed for the ICT kit (50%).

A summary of the sequence listing is shown below:

| Sequence | Sequence Identity No. |
|---|---|
| Nucleotide sequence of antigen B.4 | <400>1 |
| Amino acid sequence of antigen B.4 | <400>2 |
| Nucleotide sequence of antigen B.6 | <400>3 |
| Amino acid sequence of antigen B.6 | <400>4 |
| Nucleotide sequence of antigen B.10 | <400>5 |
| Amino acid sequence of antigen B.10 | <400>6 |
| Nucleotide sequence of antigen MMP | <400>7 |
| Amino acid sequence of antigen MMP | <400>8 |
| Nucleotide sequence of antigen C17 | <400>9 |
| Amino acid sequence of antigen C17 | <400>10 |

DETAILED DESCRIPTION OF THE PREFERRED EMBODIMENTS

The present invention is predicated in part on the identification of molecules from *Mycobacterium* species which are immunointeractive with antigen-specific molecules from humans, animals or birds which have been infected with the *Mycobacterium* species or its relative or extracts thereof or following administration to humans, animals or birds the molecule itself or in combination with a mixture of molecules. Detection of the molecules from *Mycobacterium* species or antibodies thereto is indicative of the presence of the particular species of *Mycobacterium* and hence has both diagnostic and therapeutic implications.

Accordingly, one aspect of the present invention provides an isolated polypeptide or a derivative, homologue, analogue or functional equivalent thereof wherein said polypeptide is obtainable from a species of *Mycobacterium* and which polypeptide is immunointeractive with sera from a human, animal or avian species exposed to said species of *Mycobacterium* or its relative or antigenic parts thereof but which polypeptide is substantially not immunointeractive with sera from a human, animal or avian species not prior exposed to said species of *Mycobacterium* or its relative or its antigenic parts.

For the purposes of exemplifying the present invention, the preferred species of *Mycobacterium* is *M. tuberculosis*. However, the present invention also extends to its relatives, *Mycobacterium bovis* and *Mycobacterium africanum*. In addition, the present invention further contemplates other mycobacteria including but not limited to *Mycobacterium avium, Mycobacterium microti, Mycobacterium leprae, Mycobacterium lepraemurium, Mycobacteria paratuberculosis, Mycobacterium ulcerans, Mycobacterium marinum, Mycobacterium smegmatis, Mycobacterium intracellulare, Mycobacterium xenopi, Mycobacterium chelonei, Mycobacterium fortuitum, Mycobacterium farcinogenes, Mycobacterium flavum, Mycobacterium haemophitum, Mycobacterium kansasii, Mycobacterium phlei, Mycobacterium scrofulaceum, Mycobacterium senegalense, Mycobacterium simiae, Mycobacterium thermoresistible,* and *Mycobacterium xenopi*. Accordingly, in a preferred embodiment, the present invention is directed to an isolated polypeptide or a derivative, homologue, analogue or functional equivalent thereof wherein said polypeptide is obtainable from *M. tuberculosis* or a related organism and which polypeptide is immunointeractive with sera from a human previously exposed to *M. tuberculosis* or an antigenic extract therefrom but is substantially not immunointeractive with human sera not previously exposed to *M. tuberculosis* or a antigenic extract thereof.

In the comparison to human sera not previously exposed to *M. tuberculosis*, this does not exclude sera from subjects previously exposed to other species of *Mycobacterium* or other genera having biochemical or genetic but not epidemeological properties related to *M. tuberculosis*.

The sera preferably contains antibodies to the polypeptide of the present invention. The present invention extends, however, to other antigen-specific molecules or components of the immune system having antigen specificity including but not limited to cells carrying surface immunoglobulins specific to the polypeptide and T-cell derived antigen binding molecules (TABMs).

Preferably, the immunointeraction is an interaction between an antibody in the sera of a person previously exposed to *M. tuberculosis* or a related organism or an antigen containing extract therefrom and the polypeptide or its antigenic derivatives from *M. tuberculosis*. The term "related" in this context means another species of *Mycobacterium* or strain of *M. tuberculosis* which is associated with a similar disease as caused or exacerbated by *M. tuberculosis*.

Generally, a person "previously" exposed to *M. tuberculosis* or its antigen extract, is a person exhibiting immunological memory of the interaction and, hence, carrying antibodies in the sera to an antigen of *M. tuberculosis*. Conveniently, the sera are from patients with active pulmonary or extra-pulmonary tuberculosis.

As stated above, reference to a relative to *M. tuberculosis* includes various strains of *M. tuberculosis* as well as different species of *Mycobacterium* which contain the same polypeptide or an antigenically related polypeptide. Examples of related species include *M. bovis* and *M. africanium*. Such related strains or species would induce or be associated with similar disease conditions induced by *M. tuberculosis*.

Accordingly, another aspect of the present invention provides an isolated polypeptide obtainable from *M. tuberculosis* or related organism or a derivative, homologue, analogue or chemical equivalent of said polypeptide which polypeptide is immunointeractive with sera from a human patient with active pulmonary or extra-pulmonary tuberculosis but is substantially not immunointeractive with sera from a subject not previously infected with *M. tuberculosis* or sera from a subject who otherwise has no immunological memory for said polypeptide or antigenic derivatives thereof.

In a preferred embodiment, the polypeptides of the present invention from *M. tuberculosis* range in molecular weight from about 5 kDa to about 100 kDa. More preferably, the polypeptides have a molecular weight range of from about 10 to 20 kDa, 28 to 38 kDa, 38 to 48 kDa, 53 to 63 kDa and 55 to 65 kDa.

In a most preferred embodiment, the molecular weight of the polypeptides are selected from 16±3, 33±3, 38±3, 55±3 and 56±3 kDa.

Accordingly, another aspect of the present invention is directed to a polypeptide having a molecular weight selected from about 5 kDa to about 100 kDa or a derivative, homologue, analogue or functional equivalent thereof said polypeptide obtainable from *M. tuberculosis* and wherein the polypeptide is immunointeractive with sera from a patient with active pulmonary or extra-pulmonary tuberculosis but substantially not immunointeractive with sera from a subject who does not have active pulmonary or extra-pulmonary tuberculosis.

More particularly, the present invention provides a polypeptide having a molecular weight selected from 16±3, 33±3, 38±3, 55±3 and 56±3 kDa or a derivative, homologue, analogue or functional equivalent thereof said polypeptide obtainable from *M. tuberculosis* and wherein polypeptide is immunointeractive with sera from a patient with active pulmonary or extra-pulmonary tuberculosis but substantially not immunointeractive with sera from a subject who does not have active pulmonary or extra-pulmonary tuberculosis.

The present is particularly exemplified in relation to *Mycobacterium* antigens B.4, B.6, B.10, MMP and C17 having amino acid sequences and corresponding nucleotide sequence as set forth in SEQ ID NO:1, SEQ ID NO:3, SEQ ID NO:5, SEQ ID NO:7, SEQ ID NO:9 respectively.

Accordingly, another aspect of the present invention provides a polypeptide comprising an amino acid sequence selected from SEQ ID NO:2, SEQ ID NO:4, SEQ ID NO:6, SEQ ID NO:8, SEQ ID NO:10 or an amino acid sequence having at least 60% similarity to any one of said sequences.

Yet a further aspect of the present invention provides a polypeptide encoded by a nucleotide sequence selected from SEQ ID NO:1, SEQ ID NO:3, SEQ ID NO:5, SEQ ID NO:7, SEQ ID NO:9 or a nucleotide sequence having at least 60% similarity to any one of said sequences or a nucleotide sequence capable of hybridizing to any one of said sequences under low stringency conditions at 42° C.

Even yet a further aspect of the present invention provides a nucleotide sequence selected from SEQ ID NO:1, SEQ ID NO:3, SEQ ID NO:5, SEQ ID NO:7, SEQ ID NO:9 or a nucleotide sequence having at least 60% similarity to any one of said sequences or a nucleotide sequence capable of hybridizing to any one of said sequences under low stringency conditions at 42° C.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity. Any number of programs are available to compare nucleotide and amino acid sequences. Preferred programs have regard to an appropriate alignment. One such program is Gap which considers all possible alignment and gap positions and creates an alignment with the largest number of matched bases and the fewest gaps. Gap uses the alignment method of Needleman and Wunsch (19). Gap reads a scoring matrix that contains values for every possible GCG symbol match. GAP is available on ANGIS (Australian National Genomic Information Service) at website http://mell.angis.org.au.

Reference herein to a low stringency at 42° C. includes and encompasses from at least about 1% v/v to at least about 15% v/v formamide and from at least about 1M to at least about 2M salt for hybridisation, and at least about 1M to at least about 2M salt for washing conditions.

Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions. In general, washing is carried out $T_m$=69.3+0.41 (G+C)% (17). However, the $T_m$ of a duplex DNA decreases by 1° C. with every increase of 1% in the number of mismatch base to pairs (18).

The present invention also provides genetic constructs comprising nucleic acid molecules encoding the *Mycobacterium* antigens as well as cells transformed with same. Examples of such cells include *Mycobacterium* cells, *E. coli*, insect cells, yeast cells, mammalian cells and plant cells.

The term "derivative" includes mutants, fragments and parts of the polypeptide of the present invention including single and multiple amino acid substitutions, additions and/or deletions to the naturally occurring amino acid sequences.

Preferably, the derivative is an antigenic fragment of the subject polypeptide meaning it contains an epitope required for an antibody in the sera of a patient with active pulmonary or extra-pulmonary tuberculosis to bind to the antigenic fragment.

A homologue includes functionally, structurally or stereochemically similar polypeptides from other species of *Mycobacterium* or other genera of bacteria. A homologue as contemplated herein includes a mimotope. The use of mimotopes is quite useful in competing with *Mycobacterium* polypeptide antigens for binding to antibodies. This competition may then be used to determine the concentration of polypeptides.

Analogues and mimetics include molecules which contain non-naturally occurring amino acids and which do not contain amino acids but nevertheless behave functionally the same as the polypeptide. Natural product screening is one useful strategy for identifying analogues and mimetics. Natural product screening involves screening environments such as bacteria, plants, riverbeds, seabeds, aquatic environments, coral and antarctic or arctic environments for naturally occurring molecules which mimic, agonise or antagonise the function of the *Mycobacterium* polypeptide of the present invention.

Chemical libraries may also be screened for synthetic mimetics, agonists, antagonists or chemical analogues of the subject polypeptides.

Analogues of the subject peptides contemplated herein also include modifications to side chains, incorporation of unnatural amino acids and/or their derivatives during peptide synthesis and the use of crosslinkers and other methods which impose conformational constraints on the peptide molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid contemplated herein is shown in Table 1.

TABLE 1

| Non-conventional amino acid | Code |
|---|---|
| α-aminobutyric acid | Abu |
| α-amino-α-methylbutyrate | Mgabu |
| aminocyclopropanecarboxylate | Cpro |
| aminoisobutyric acid | Aib |
| aminonorbornylcarboxylate | Norb |
| cyclohexylalanine | Chexa |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |
| D-serine | Dser |

TABLE 1-continued

| Non-conventional amino acid | Code |
|---|---|
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl)carbamylmethyl)glycine | Nnbhm |
| 1-carboxy-1-(2,2-diphenylethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |

TABLE 1-continued

| Non-conventional amino acid | Code |
|---|---|
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl)carbamylmethyl)glycine | Nnbhe |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

All these types of modifications may also be important to stabilise the subject polypeptide if used in a diagnostic or therapeutic test.

The present invention further contemplates functional equivalents of the subject polypeptides. Functional equivalents may not necessarily be derived from the polypeptides themselves but may share certain conformational similarities. Alternatively, functional equivalents may be specifically designed to mimic certain physiochemical properties of the polypeptides. Functional equivalents may be chemically synthesised or may be detected following, for example, natural product screening.

Reference to the subject polypeptide from *Mycobacterium* species should be read as including reference to all forms of the polypeptide including, by way of example, isoforms or monomeric, dimeric or multimeric forms or peptide fragments of the polypeptide as well as derivatives, homologues, analogues and functional equivalents thereof.

The polypeptide of the present invention may contain a range of other molecules fused, linked, bound or otherwise associated to the polypeptide such as amino acids, lipids, carbohydrates or other peptides, polypeptides or proteins.

The polypeptides of the present invention may be a purified naturally occurring molecule, produced by chemical synthetic techniques or may be produced by recombinant DNA technology.

The present invention further contemplates a method of isolating a polypeptide from *Mycobacterium* species said method comprising culturing cells of said *Mycobacterium* species in a growth medium to increase the number of cells to a sufficient population, harvesting said cells and subjecting said cells to protein extraction techniques to extract protein from said cells, fractionating the extracted protein and subjecting said protein to binding analysis with antibodies to said *Mycobacterium* species or antigenic portions thereof and isolating the polypeptides to which antibodies interact.

Preferably, the *Mycobacterium* species in *M. tuberculosis*.

Preferably, the growth medium is Lowenstein-Jensen medium.

Preferably, fractionation of total polypeptides from *M. tuberculosis* is conducted by SDS-PAGE.

Preferably, the binding analysis in a Western blot analysis.

The isolated polypeptide bands are then generally subjected to N-terminal, C-terminal or internal amino acid sequencing. Nucleotide probes are then produced and cDNA or genomic libraries screened for genetic sequences encoding the isolated polypeptides.

In a particularly preferred embodiment, the polypeptide of the present invention comprises an N-terminal amino acid sequence substantially as set forth in one of SEQ ID NOs:1 to 10 or an amino acid sequence having at least about 70% similarity thereto.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity. Any number of programs are available to compare nucleotide and amino acid sequences. Preferred programs have regard to an appropriate alignment. One such program is Gap which considers all possible alignment and gap positions and creates an alignment with the largest number of matched bases and the fewest gaps. Gap uses the alignment method of Needleman and Wunsch (9). Gap reads a scoring matrix that contains values for every possible GCG symbol match. GAP is available on ANGIS (Australian National Genomic Information Service) at website http://mell.angis.org.au.

Yet another aspect of the present invention is directed to genetic sequences encoding the polypeptide herein described.

Accordingly, another aspect of the present invention provides an isolated nucleic acid molecule comprising a sequence of nucleotides encoding or complementary to a sequence encoding a polypeptide obtainable from a species of *Mycobacterium* and which polypeptide is immunointeractive with sera from a human, animal or avian species exposed to said species of *Mycobacterium* or its relative or antigenic parts thereof but which polypeptide is substantially not immunointeractive with sera from a human, animal or avian species not prior exposed to said species of *Mycobacterium* or its relative or its antigenic parts.

The preferred *Mycobacterium* species in *M. tuberculosis* although the present invention extends to any species of *Mycobacterium* or its relatives.

Preferably, the nucleotide sequence encodes an amino acid sequence substantially as set forth in one of SEQ ID NOs:1 to 10 or an amino acid sequence having at least about 70% similarity thereto.

The nucleic acid molecule of this aspect of the present invention may be cDNA, genomic DNA or mRNA or cDNA/genomic DNA or DNA/RNA hybrids. The nucleotide sequence may encode the amino acid sequence of the naturally occurring polypeptide or it may encode a mutant, fragment, part or other derivative of the polypeptide. Accordingly, the nucleotide sequence may contain one or more nucleotide substitutions, deletions and/or additions to the naturally occurring sequence.

The nucleotide acid molecule of the present invention may be linear or covalently closed single or double stranded molecules, alone or as part of a genetic construct such as an expression vector and/or purification vector.

Still another aspect of the present invention is directed to antibodies to the subject polypeptides or their derivatives, homologues, analogues, mimetics and functional equivalents thereof. Such antibodies may be monoclonal or polyclonal. Where the derivatives are peptides, these may first need to be associated with a carrier molecule in order to induce antibody formation.

The antibodies of the present invention are particularly useful as therapeutic or diagnostic agents. For example, specific antibodies can be used to assist in screening for polypeptides in immunoassays or used as antagonists to inhibit polypeptide activity under certain circumstances. Techniques for such immunoassays are well known in the art and include, for example, sandwich assays and ELISA. Knowledge of polypeptide levels may be important for monitoring certain therapeutic protocols.

As stated above, the antibodies may be monoclonal or polyclonal antibodies. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies.

As stated above, specific antibodies can be used to screen for the subject polypeptides. The latter would be important, for example, as a means for screening for levels of polypeptides in a cell extract or other biological fluid or purifying polypeptides made by recombinant means from culture supernatant fluid. The antibodies may also be used to screen for the presence of particular *Mycobacterium* polypeptides. The presence of *M. tuberculosis* polypeptides, for example, is indicative of tuberculosis.

It is within the scope of this invention to include any second antibodies (monoclonal, polyclonal or fragments of antibodies or synthetic antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of polypeptide.

Both polyclonal and monoclonal antibodies are obtainable by immunization with the *Mycobacterium* polypeptides either type is utilizable for immunoassays. The methods of obtaining both types of sera are well known in the art. Polyclonal sera are less preferred but are relatively easily prepared by injection of a suitable laboratory animal with an effective amount of polypeptide, or antigenic parts thereof, collecting serum from the animal and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates a method for detecting a subject polypeptide in a biological sample from a subject or culture supernatant flow or other source said method comprising contacting said biological sample with an antibody specific for said polypeptide or its derivative, homologue, analogue, mimetic or chemical equivalent thereof for a time and under conditions sufficient for an antibody-polypeptide complex to form, and then detecting said complex.

The presence of the polypeptide may be accomplished in a number of ways such as by Western blotting and ELISA procedures. A wide range of immunoassay techniques are available as can be seen by reference to U.S. Pat. Nos.

4,016,043, 4,424,279 and 4,018,653. These include both single-site and two-site or "sandwich" assays of the non-competitive types, as well as in the traditional competitive binding assays. These assays also include direct binding of a labelled antibody to a target.

A number of variations of the sandwich assay technique exist, and all are intended to be encompassed by the present invention. Briefly, in one form of forward assay, an unlabelled *Mycobacterium* polypeptide is immobilized on a solid substrate and a sample of animal (e.g. human) sera to be tested brought into contact with the bound molecule. After a suitable period of incubation, for a period of time sufficient to allow formation of a polypeptide-antibody complex, a second antibody specific to animal (e.g. human) immunoglobulin, labelled with a reporter molecule capable of producing a detectable signal is then added and incubated, allowing time sufficient for the formation of another complex of polypeptide-antibody labelled antibody. Any unreacted material is washed away, and the presence of polypeptide specific antibody determined by observation of a signal produced by the reporter molecule or the anti-animal (e.g. human) immunoglobulin. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. The method of this aspect of the present invention may readily be adapted for screening for *Mycobacterium* polypeptide by, for example, immobilizing an antibody specific for the polypeptide.

Immobilization of polypeptide or antibody either covalent or passive binding to a solid surface. The solid surface is typically glass or a polymer, the most commonly used polymers being cellulose, nitrocellulose, polyacrylamide, nylon, polystyrene, polyvinyl chloride or polypropylene. The solid supports may be in the form of tubes, beads, discs of microplates, cover slips, slides or any other surface suitable for conducting an immunoassay. The binding processes are well-known in the art and generally consist of cross-linking covalently binding or physically adsorbing the polypeptide or antibody to the solid support. An aliquot of the sample to be tested is then added to the solid phase complex and incubated for a period of time sufficient (e.g. 2–40 minutes or overnight if more convenient) and under suitable conditions (e.g. from room temperature to about 37° C.) to allow binding of the polypeptide or antibody to its immobilized ligand. Following the incubation period, the solid phase is washed and dried and incubated with an antibody specific for a portion of the polypeptide or antibody. This antibody is linked to a reporter molecule which is used to indicate the binding of the antibody to its ligand.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes), chemiluminescent molecules colloidal material and precious metals such as gold.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, luciferase, glucose oxidase, β-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates which yield a fluorescent product rather than the chromogenic substrates noted above. In all cases, the enzyme-labelled antibody is added to the antibody-polypeptide complex, allowed to bind, and then the excess reagent is washed away. A solution containing the appropriate substrate is then added to the complex of antibody-polypeptide-antibody. The substrate will react with the enzyme linked to the antibody, giving a qualitative visual signal, which may be further quantitated, usually spectrophotometrically, to give an indication of the amount of polypeptide which is present in the sample. The reporter molecule also extends to use of cell agglutination or inhibition of agglutination such as red blood cells on latex beads and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in the EIA, the fluorescent labelled antibody is allowed to bind to the antibody-polypeptide complex. After washing off the unbound reagent, the remaining tertiary complex is then exposed to the light of the appropriate wavelength the fluorescence observed indicates the presence of the polypeptide of interest. Other reporter molecules, such as radioisotope, chemiluminescent or bioluminescent molecules, may also be employed.

The polypeptides of the present invention and antibodies thereto are useful for detecting *Mycobacterium* infection and/or disease or other conditions associated with *Mycobacterium*. The presence of *Mycobacterium* in environmental samples may also be accomplished. In a particularly preferred embodiment, polypeptides derived from *M. tuberculosis* are detected. In this case, the polypeptides are particularly useful in detecting tuberculosis.

Accordingly, another aspect of the present invention contemplates a method for detecting the presence of *M. tuberculosis* such as in a patient suffering from tuberculosis said method comprising contacting a biological sample from a patient or subject with an antibody specific for a polypeptide from said *M. tuberculosis* and detecting a complex between said polypeptide and said antibody.

In an alternative embodiment there is provided a method for detecting the presence of *M. tuberculosis* such as in a patient suffering from tuberculosis said method comprising contacting a sera sample from a patient or subject with a polypeptide from *M. tuberculosis* and detecting a complex between said polypeptide and an antibody in said sera.

The polypeptide-antibody complex may be detected by any convenient means. One particularly useful method is to detect the complex using an anti-immunoglobulin labelled with a reporter molecule such as but not limited to colloidal gold, an enzyme, a radioactive isotope or a fluorescent compound.

In a particularly preferred embodiment, one or more polypeptides from *M. tuberculosis* are immobilized onto a solid support. Sera from a patient suspected of having exposure to *M. tuberculosis* are then brought into contact with immobilized polypeptides(s). After a time sufficient from an immobilized polypeptide-antibody complex to form, unbound material is washed away and an anti-human immunoglobulin labelled with a reporter molecule is brought into contact to bind to human antibodies in the sera of a patient which have bound to the immobilized *M. tuberculosis* polypeptide. The presence of an identifiable signal from the reporter molecule indicates the presence of the polypeptide and of *M. tuberculosis*. This is a particularly convenient means of identifying tuberculosis or a likelihood of tuberculosis or its possible development.

Reference herein to "tuberculosis" includes reference to pulmonary and extra-pulmonary tuberculosis.

There are many different ways of conducting this assay. For example, an application matrix comprising absorable material such as filter paper and the like may comprise an application region, a *M. tuberculosis* polypeptide region and detection region. In the arrangement, sera from a patient or subject to be tested are applied to the application region and allowed to passage (i.e. "wick") along the application matrix through a region comprising impregnated *M. tuberculosis* polypeptide or its derivatives, homologues, analogues or antigenic equivalents. If antibodies are present in the sera specific for the polypeptide, a complex will form. This complex may be detected directly by the application of an anti-human immunoglobulin antibody labelled with a reporter molecule or the complex may be allowed to migrate into a third region impregnated with anti-human immunoglobulin antibody labelled with a reporter molecule. The identifiable signal produced by the reporter molecule can then be detected in that third region or in a fourth region where the sera-polypeptide-labelled antibody is permitted to concentrate.

In a particularly preferred embodiment, there is provided an assay device for *M. tuberculosis* comprising a solid support having immobilized thereon one or more polypeptides obtainable from *M. tuberculosis* or derivatives, homologues, analogues or antigenic equivalents thereof and a portion of said solid support adapted for receiving a sample from a human subject to be tested wherein said sample would contain an antibody specific for said *M. tuberculosis* polypeptide if said subject has been exposed to *M. tuberculosis* wherein upon contact between the antibody from the subject and the immobilized polypeptide, a complex forms and said complex is detected by an anti-human immunoglobulin labelled with a reporter molecule.

Yet another preferred assay technique comprises applying sera from a subject to be tested to an application matrix and allowing the sera to passage (i.e. "wick") along the matrix and into an area impregnated with recombinant polypeptides from *Mycobacterium* species and in particular *M. tuberculosis*. A complex forms between antibodies in the sera and the polypeptides and these complexes as well as free antibodies and free polypeptides continue to migrate to a region comprising anti-human antibodies labelled a reporter molecule such as, for example, gold. The passaging molecules then enter a region with reduced pore size such as an area containing nitrocellulose. The molecules which are not part of a complex pass through this region whereas complexes of antibodies and polypeptides tend to concentrate as a band in front of the region with reduced pore size (e.g. nitrocellulose region). If the label is gold the line of complexes is pink or like colour or black. If silver stained or blue when the label is coloured latex particles.

Regardless of the assay procedure, and whether or not "wicking" is involved, one particularly useful procedure for detecting antibody-polypeptide interactivity is through electronic means such as described in U.S. Pat. No. 5,580,794.

All such electronic detection means are contemplated for use in accordance with the present invention. For example, interaction between certain molecules may lead to the production of an electrical signal which in turn, via a signal processor, correlates with the amount of interaction of amount of certain components of an interaction.

The present invention extends to the detection of a single type or species of *Mycobacterium* polypeptide as well as to the detection of a combination of *Mycobacterium* polypeptides. The detection of combinations of antigens may be accomplished, for example, by using a multiple array of antibodies.

The identification and isolation of the *Mycobacterium* species polypeptide of the present invention further permits the development of therapeutic protocols for generating, for example, an immune response directed to *Mycobacterium* species. Preferably, the *Mycobacterium* species is *M. tuberculosis.*

Accordingly, the present invention contemplates a composition comprising one or more polypeptides for *Mycobacterium* species or a derivative, homologue, analogue, mimetic or chemical equivalent thereof and one or more pharmaceutically acceptable carriers and/or diluents. These components are referred to as the "active ingredients". Preferably, the polypeptides are from *M. tuberculosis* and the composition is capable of inducing an immune response against *M. tuberculosis.*

The compositions suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The preventions of the action of microorganisms can be brought about by various antibacterial and antifungal agents, for example, parabens, chlorobutanol, phenol, sorbic acid, thimersal and the like. In many cases, it will be preferable to include isotonic agents, for example, sugars or sodium chloride. Prolonged absorption of the injectable compositions can be brought about by the use in the compositions of a gents delay ing absorption, for example, aluminum monostearate and gelatin.

Sterile injectable solutions are prepared by incorporating the polypeptide or other active compounds in the required amount in the appropriate solvent with various of the other ingredients enumerated above, as required, followed by filtered sterilization. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

Pharmaceutically acceptable carriers and/or diluents include any and all solvents, dispersion media, coatings, antibacterial and antifungal agents, isotonic and absorption delaying agents and the like.

The principal active ingredient, i.e. the polypeptide, will be present in the composition in an amount effective to induce an immune response. The composition may permit, for example, 0.01 μg to about 2000 mg/kg body weight.

The pharmaceutical composition may also comprise genetic molecules such as a vector capable of transfecting target cells where the vector carries a nucleic acid molecule capable of modulating expression of genes encoding a polypeptide from *Mycobacterium* species. The vector may, for example, be a viral vector.

The present invention further contemplates the use of a polypeptide from *Mycobacterium* species such as *M. tuberculosis* or a derivative, homologue, analogue, mimetic or chemical equivalent thereof in the manufacture of a medicament for the treatment of *Mycobacterium* infection such as tuberculosis.

The present invention is further described by the following non-limiting Examples.

EXAMPLE 1

Extraction of *M. Tuberculosis* Total Protein

*Mycobacterium tuberculosis* cells (ATCC 27294) were cultured in BBL MycoFlask containing Lowenstein-Jensen medium at 37° C. with 10% v/v $CO_2$. After 2 weeks, the confluent cells were harvested, washed and resuspended in an equal volume of MilliQ $H_2O$. The cell suspension was heated to 90° C. for 2 h after which it was frozen at −20° C. overnight. Thawed cells were sonicated for 2–3 min and pelleted at 14,000 rpm for 10 min. Extraction of total protein was performed in 8M urea (equal ratio of weight of cells to volume of 8M urea). The cell suspension was vortexed at room temperature for 20 min heated at 90° C. for 2 min. Insoluble cellular debris was pelleted at 14,000 rpm for 10 min and the supernatant containing the extracted total protein was kept at −20° C. until further use.

EXAMPLE 2

SDS-PAGE Analysis and Immunological Analysis

The total protein extract from *M. tuberculosis* was fractionated on a 7.5% w/w SDS-PAGE (10) and transferred onto a nitrocellulose membrane by the conventional western blot method (11). Strips containing the Western blotted *M. tuberculosis* total proteins were immunoscreened with pooled sera from 9 patients having active tuberculosis (TB) and pooled sera from 7 normal non-infected individuals, respectively. Detection was carried out using the goat anti-human Ig conjugated with alkaline phosphatase (Harlan Sera lab,UK).

EXAMPLE 3

N-Terminal Sequencing of *M. Tuberculosis* Bands

Several individual protein bands (Mwt ranging from 10 to 160 kDa), which reacted positively in the immunoscreening, were excised from a preparative 7.5% w/v SDS-polyacrylamide gel, and concentrated on a long stacking gel (7 cm of 4% w/v stacking gel, 5 cm of 10% w/v resolving gel). After concentration, the protein bands were blotted onto a PVDF membrane and subsequently stained with Coomassie Brilliant Blue R-250. The stained protein bands were then excised from the membrane and used for N-terminal microsequencing. In addition, some of the protein bands were also blotted onto nitrocellulose membrane to repeat immunoscreening using the same pooled sera samples as previously described.

EXAMPLE 4

Screening the EcoR1 Lambda ZAP Phage Expression Library of *M. Tuberculosis* Genomic DNA An expression library of EcoR1 restricted genomic DNA of *M. tuberculosis* was constructed in lambda ZAP Phage expression vector (according to the protocol by Stratagene (12)). The resultant library have 98% of recombinants ($2\times10^6$ pfu/μg arms) and insert sizes ranging from 0.7–2 kb, observed in excised recombinant plasmids restricted with EcoR1 restriction enzyme. A lawn of XL1-MRF' cells infected with about $2\times10^4$ pfu of the phage stock was prepared on a 150 mm plate, and incubated inverted, for 6–7 hr at 42° C. The lawn was then overlaid with a Hybond-C filters, presoaked in 1 mM IPTG for induction of protein expression and were incubated at 37° C. for 4 hr, causing the transfer of expressed TB recombinant proteins from the plaques onto the membrane. The plate and filter were indexed for matching of corresponding plate and filter positions. About 20 plates were prepared for the library and as a negative control, a lawn of host cells infected with $2\times10^4$ pfu of the non-recombinant lambda ZAP phage was used instead.

Filters were washed twice in TBST buffer (10 mM Tris, ph7.5, 300 mM NaCl, 0.005% v/v Tween 20), blocked in 5% w/v skim milk in TBST, washed again in TBST and used to screen against 4 pooled active TB sera and pooled normal sera, respectively. The preabsortion regime for the pooled sera was as follows: negative control filters containing proteins from induced lambda ZAP phage vector in the bacteria host was used. Pooled sera (diluted 1:100 in 1% w/v skim milk/TBST) was incubated (15 ml/filter) for 2 hr at RT after which sera was diluted to 1:200 in 1% w/v skim milk/TBST and transferred to a fresh control filter for overnight preabsorption. Screening was as follow: filters containing the expressed recombinant proteins from the phage library were incubated with pre-absorbed human sera for 2 hr, rocking at RT and washed three times in TBST. Secondary antibody of anti-human Ig—alkaline phosphatase conjugated (diluted 1:1000 in 1% w/v skim milk/TBST) was added and allowed to incubate for 1 hr. After a final wash, the detection was by colormetric, using NBT/BCIP substrate. An immunoreactive recombinant clone, C17, was isolated and confirmed in the tertiary screening.

Secondary and tertiary plating: positive plaques were cored out and phage eluted in SM bufffer (13) containing 2% v/v chloroform and replated at about 100–200 pfu on a 82 mm plates. The screening steps using pooled sera were repeated to confirm the positive clones. In the tertiary screening 6 positive phage recombinants were obtained and these were subsequently subjected to plasmid excision (12). Restriction enzyme EcoR1 digestion indicated that all the clones have a 2 kb insert which was later confirmed to be identical by DNA sequencing. The clones were designated as C17 and have a 1.16 kb open reading frame (in frame with the vector ATG initiation codon) coding for a 38±3 kDa protein.

EXAMPLE 5

Cloning and Expression of Genes for the *M. Tuberculosis* Antigens

Primers were designed from the N-terminal sequences. Polymerase chain reaction (PCR) was performed using the Advantage®-GC Genomic PCR kit (Clontech), *M. tuberculosis* genomic DNA (extracted as previously described (14)) and synthetic oligonucleotides. The PCR products were cloned into the pGEMT vector (Promega) before subcloning into the pQE30 expression vector (15) (FIG. 1). Expression was carried out in $M_{15}$ *E. coli* cells, induced with 1 mM IPTG. The $M_{15}$ cells at 3 hr after induction were harvested, and cell pellet lysed in 8M urea buffer at pH6.5. The expressed recombinant protein contained a 6× histidine tag at the N-terminus which facilitated the purification with the Ni-NTA affinity column. Column washes were carried out in 8M urea buffer at pH 6.5 and pH 5.9 while subsequently elution of recombinant protein was carried out at pH4.5.

Table 2 provides the gene sizes for each TB antigen and the theoretical mass.

TABLE 2

GENE SIZE AND PHYSICAL CHARACTERISTICS OF TB ANTIGENS

| | | Theoretical* | |
|---|---|---|---|
| Antigen | Size of gene (kb) | Molecular mass | pI value |
| B.4 | 1.617 | 55.8 | 5.12 |
| B.6 | 1.560 | 55.0 | 5.03 |
| B.10 | 0.903 | 32.9 | 4.95 |
| MMP | 0.432 | 16.1 | 5.00 |
| C17 | 1.161 | 37.5 | 9.43 |

*obtained using the software "Compute pI/Mwt" from ExPASy homepage, Swiss Institute of Bioinformatics, Geneva The gene size of each TB antigen and the theoretical molecular mass and pI values as calculated from the respective deduced amino acid sequence. The resultant recombinant proteins will be approximately 1.4 to 1.5-kDa larger than the theoretical molecular mass shown, due to the 6× Histidine tag at the N-terminal.

EXAMPLE 6

SDS-PAGE and Western Blot of *M. Tuberculosis* Recombinant Antigens

A total of 27 μg of a partially purified recombinant antigen was subjected to a SDS-PAG electrophoresis at 180V for 1 hr. The recombinant antigen was transferred from the polyacrylmide gel onto a Hybond-nitrocellulose membrane (Amersham) by Western blot (11), using the BioRad Trans-Blotter (according to manufacturer's protocol). After transfer, the membrane was blocked in 5% w/v milk/TBST, air dried and stored at 4° C. until further use.

EXAMPLE 7

Screening of the Recombinant *M. Tuberculosis* Antigens Against Active (Pulmonary and Extra-Pulmonary), Inactive and Normal Sera Panels Each membrane was cut into strips (a total of 23 strips can be obtained from each blot) and each strip was used for screening with a serum sample. One strip was used as an internal positive of known serum sample which reacted with the recombinant protein antigen and another was used to probe with the commercially available anti-RGSH is probe (QIAGEN). Sera samples were diluted to 1:100 in 1% w/v milk/TBST. Screening was carried out in tubes individually (2 strips/tube) and 3 ml of diluted serum/tubes for 1 hr with rocking at room temperature. The strips were then washed 3 times in TBST and were incubated with Goat anti-human Ig alkaline phosphatase conjugated (Harlan Sera lab) for 1 hr with rocking at room temperature. The strips were washed 3 times in TBST and allowed to develop in 1 ml of NBT/BCIP substrate (BioRad) for 4 mins.

Reactivity of recombinant protein to patient sera was interpreted based on the intensity of band observed, ie. negative, + and 2+; the later two were taken as a positive. Faintly stained bands were scored negative.

Using the above screening procedure, the five recombinant antigens were screened against a total of 85 human sera; 43 were from bacteriologically confirmed tuberculosis patients [23 pulmonary, 20 extra-pulmonary]; 22 inactive samples (with skin PPD tve but smear and bacteria culture negative); and 20 sera samples of uninfected individuals previously vaccinated with BCG. All sera were stored at −70° C. before use.

EXAMPLE 8

Identification of *M. Tuberculosis* Polypeptides

Immunological analysis of Western blotted *M. tuberculosis* total proteins gave 9 protein bands which reacted with the 9 pooled active sera but not with the 7 pooled normal sera. The respective bands were concentrated on a long stacking gel and excised. Excised protein bands were reactive with the pooled active sera but not with pooled normal sera, thus confirming the authenticity of these excised proteins as initially observed in the primary screening (FIG. 2). These proteins were identified by homology searches against protein sequence databases and the result gave a high percentage of homology to *Mycobacterium* proteins (FIG. 3). Primers for PCR were constructed to isolate gene that codes for proteins which gave the high homology (FIG. 1). B.4, B.6, B.10, C17 and MMP were among the genes in addition to B.5 (16), B.9 and 38 kDa isolated from *M. tuberculosis* genomic DNA.

The QIAGEN expression system was selected by the inventors for cloning and expression of the corresponding genes. This system utilizes the pQE30 vector whereby the expressed protein can be purified through a simple one step affinity chromatography and insoluble recombinant proteins can be purified under denaturation conditions (FIG. 1). Expression of recombinant proteins can be immunodetected by the commercially available anti-RGSHis. In addition, the 6×His tag is non-immunogenic and thus the purified recombinant protein can be used directly in a Western blot format for screening against the sera.

From the expression studies, B.4, B.5, B.9, MMP and 38 kDa gave high level of expression whereas B.6, B.10 and C17 expression level was low. All of these recombinant proteins were detected by anti-RGSHis. In addition, most of the recombinant proteins were insoluble except for B.5 and C 17 which was soluble. As such the format of choice for our initial screening was on a Western format.

Results of Western screening and the intensity of band observed on the strip is as shown in FIG. 4. Percentage of reactivity were calculated based on the number of sera which gave positive (+ or 2+observed on the strip) divided by the number of sera sample screened. FIG. 5 shows the percentage of reactivity of recombinant TB antigens against different sera panels. A known 38 kDa antigen (7, 8) of *M. tuberculosis* was included in the screening. The gene (GeneBank Accession # M30046) for this antigen was cloned, expressed in pQE30 and partially purified. Also shown are the percentages of reactivity of sera samples detected by a commercially available rapid TB diagnostic kit from. ICT (Amrad).

Analysis of the screening result is as shown in FIG. 5 and FIG. 6. B.6, B.9, B. 10, C17, MMP and 38 kDa antigens showed no reactivity to the sera from uninfected individuals whereas B.4 and B.5 reacted to 5% and 25% of this panel respectively. B.4 and B.5 may have some epitopes which are recognised by antibodies present in uninfected animals. All of these recombinant antigens showed some reactivity to sera from the active TB panel, both pulmonary and extra-pulmonary. B.6 (52.2%) and B. 10 (26.1%) seems to be specifically reactive to active pulmonary samples whereas MMP (25%) is specific to extra-pulmonary samples. All of the recombinant samples, except for B.5 and have low reactivity (<25%) to the inactive sera panel. This is important because a good seriological diagnostic marker would be one that allow differentiation of normal and individuals having previous infection of TB (inactive) from individuals with active tuberculosis.

Overall, the percentage of reactivity to sera panels increased when more recombinant antigens were included in the combination. This is in accordance with the observation that sensitivity increases with the number of antigens used for screening. Combinations including all recombinant antigens (B.4+B.5+B.6+B.9+B.10+C17+MMP+38 kDa) gave a sensitivity of more than 90%. However the reactivity to inactive sera samples was also high (36%). Results indicate that the best combination of antigens to use is one that include B.6, B.10, B.4, MMP and C17 which gives a sensitivity of 60–70% to active sera, both pulmonary and extra-pulmonary. Specificity for this combination is 95% but reaches to 100% if excluding B.4 which as indicated earlier exhibited 5% reactivity to sera from uninfected individuals.

Comparison of reactivity against the different sera panel for the combination of all the recombinant TB antigens compared to the ICT TB diagnostic kit. The graph shows that the percentage of reactivity for the active sera panel (pulmonary and extra-pulmonary) is higher than that observed for the kit.

Combination of antigens (B.6+B.10+MMP+38 kDa) gave a sensitivity (60–70%) higher than that observed for the ICT kit (50%); the reactivity to inactive panel is comparable to that for ICT (FIG. 9). As this is not an optimized assay, the sensitivity and specificity can be increased further using a panel of combined recombinant antigens which includes B.4, B.6, B.10, MMP and C17.

EXAMPLE 9

Determination of Nucleotide and Amino Acid Sequences of *Mycobacterium* Antigens Nucleotide sequences and corresponding amino acid sequences were determined for antigens B.4, B.6, B.10, MMP and C17 and are shown in SEQ ID NO:1, SEQ ID NO:3, SEQ ID NO:5, SEQ ID NO:7, SEQ ID NO:9 respectively.

Those skilled in the art will appreciate that invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

1. Davis B. D. et al, *Microbiology,* 2nd Edition, Harper International Edition. Harper & Row Publishers. pp 844–869, 1973.
2. Murray C. J. L, et al, *Bull Int Union Tuberc Lung Dis* 65: 6–24, 1990.
3. Shinnick T M et al, *Clin Infect Dis* 21: 291–299, 1995.
4. Beige J, et al, *J Clin Microbiol,* 33: 90–95, 1995.
5. Banica D., et al, *Pneumoftiziologia,* 43: 173–177, 1994.
6. Bothamley G H *Eur Respir J Suppl* 20: 676S–688S, 1995.
7. Andersen et al, *Infect. Immun,* 57: 2481–2488, 1989.
8. Wilkinson et al., *J. Clin Micro,* 35: 553–557, 1997.
9. Needleman and Wunsch *J. Mol. Biol.* 48: 443–453, 1970.
10. Laemmnli, et al, *Nature* (*London*), 227: 680–685, 1970.
11. Towbin H, et al, *Proc. Natl. Acad. Sci.* USA 76: 4350–4354.
12. ZAP Express™cDNA Synthesis Kit, Manual, Stratagene Cloning systems.
13. Maniatis et al, "Molecular Cloning: a laboratory manual. Cold Spring harbor Laboratory, Cold Spring Harbor, N.Y. (1982).
14. Parra C. A, et al., *Infect. & Immun;* 59: 3411–3417, 1991.
15. QIAGEN GmbH and QIAGEN Inc. The QIAexpressionist—The high level expression & protein purification system.
16. Shinnick et al., *J. Bacteriol* 169:1080–1088,1987.
17. Marmur and Doty *J. Mol. Biol.* 5: 109, 1962.
18. Bonner and Laskey *Eur. J. Biochem.* 46: 83, 1974.
19. Needleman and Wunsch *J. Mol. Biol.* 48: 443–453, 1970.

What is claimed is:

1. An isolated polypeptide comprising a polypeptide having an amino acid sequence of SEQ ID NO: 4, 6, 8 or 10, or having an amino acid sequence that is at least 70% identical to an amino acid sequence of SEQ ID NO: 4, 6, 8, 10, wherein said polypeptide exhibits reactivity of from 5 to 52.5% with antisera obtained from subjects that have been infected by a *Mycobacterium* species and wherein said polypeptide exhibits a reactivity of 0% with sera obtained from subjects that have not been previously infected by a *Mycobacterium* species.

2. An isolated polypeptide comprising a polypeptide having an amino acid sequence of SEQ ID NO: 13, 15, 17, 19 or 21, wherein said polypeptide exhibits reactivity of from 5 to 52.5% with antisera obtained from subject that have been infected by a *Mycobacterium* species and wherein said polypeptide exhibits a reactivity of 0% with sera obtain from subjects that have not been previously infected by a *Mycobacterium* species.

3. An isolated polypeptide comprising a polypeptide having an amino acid sequence of SEQ ID NO:2, or having an amino acid sequence that is at least 70 identical to an amino acid sequence of SEQ ID NO: 2, wherein said polypeptide exhibits reactivity of from 35 to 55% with antisera obtained from subjects that have been infected by a *Mycobacterium* species and wherein said polypeptide exhibits a reactivity of 5 to 25% with sera obtained from subjects that have not been previously infected by a *Mycobacterium* species.

4. An isolated polypeptide comprising a polypeptide having an amino acid sequence of SEQ ID NO: 11, wherein said polypeptide exhibits reactivity of from 35 to 55% with antisera obtained from subjects that have been infected by a *Mycobacterium* species and wherein said polypeptide exhibits a reactivity of 5 to 25% with sera obtained from subjects that have not been previously infected by a *Mycobacterium* species.

5. A composition comprising at least two polypeptides having an amino acid sequence of SEQ ID NO: 4, 6, 8 or 10, or having an amino acid sequence that is at least 70% identical to an amino acid sequence of SEQ ID NO: 4, 6, 8 or 10, wherein said composition exhibits reactivity of more than 90% with antisera obtained from subjects that have been infected by a *Mycobacterium* species.

6. A composition comprising at least two polypeptides comprising an amino acid sequence of SEQ ID NO: 13, 15, 17, 19 or 21, wherein said composition exhibits reactivity of at least 60% with antisera obtained from subjects that have been infected by a *Mycobacterium* species and wherein said composition exhibits a reactivity of 0 to 5% with sera obtained from subjects that have not been previously infected by a *Mycobacterium* species.

7. The isolated polypeptide of claim 1 that has an amino acid sequence of SEQ ID NO: 4, 6, 8 or 10.

8. The isolated polypeptide of claim 2 that has an amino acid sequence of SEQ ID NO: 13, 15, 17, 19 or 21.

9. The isolated polypeptide of claim 3 that has an amino acid sequence of SEQ ID NO: 11.

10. The isolated polypeptide of claim 4 that has an amino acid sequence of SEQ ID NO: 2.

11. The composition of claim 6, wherein said polypeptides consist essentially of the amino acid sequence of SEQ ID NO: 13, 15, 17, 19 or 21.

12. The composition of claim 5, that comprises polypeptides having the amino acid sequence of SEQ ID NO: 4, 6, 8 and 10, or sequences that are 70% identical thereto.

13. The composition of claim 5, that comprises polypeptides having the amino acid sequence of SEQ ID NO: 4, 6, 8, and 10.

14. The isolated polypeptide of claim 1, that is isolated from a *Mycobacterium* selected from the group consisting of *Mycobacterium tuberculosis, Mycobacterium avium, Mycobacterium microti, Mycobacterium leprae, Mycobacterium lepraemurium, Mycobacterium paratuberculosis, Mycobacterium ulcerans, Mycobacterium marinum, Mycobacterium amegmatis, Mycobacterium intracellulare, Mycobacterium xenopi, Mycobacterium chelonei, Mycobacterium fortuitum, Mycobacterium farcinogenes, Mycobacterium flavum, Mycobacterium haemophitum, Mycobacterium kansasii, Mycobacterium phlei, Mycobacterium scrofulaceum, Mycobacterium senegalense, Mycobacterium simiae, Mycobacterium thermoresistible*, and *Mycobacterium xenopi.*

15. The isolated polypeptide of claim 2, that is isolated from a *Mycobacterium* selected from the group consisting of the *Mycobacterium tuberculosis, Mycobacterium avium, Mycobacterium microti, Mycobacterium leprae, Mycobacterium lepraemurium, Mycobacterium paratuberculosis, Mycobacterium ulcerans, Mycobacterium marinum, Mycobacterium smegmatis, Mycobacterium intracellulare, Mycobacterium xenopi, Mycobacterium chelonei, Mycobacterium fortuitum, Mycobacterium farcinogenes, Mycobacterium flavum, Mycobacterium haemophitum, Mycobacterium kansasii, Mycobacterium phlei, Mycobacterium scrofulaceum, Mycobacterium senegalense, Mycobacterium simiae, Mycobacterium thermoresistible*, and *Mycobacterium xenopi.*

16. The composition of claim 5, wherein said polypeptides are isolated from at least one *Mycobacterium* wherein the species of *Mycobacterium* selected from *Mycobacterium tuberculosis, Mycobacterium avium, Mycobacterium microti, Mycobacterium leprae, Mycobacterium lepraemurium, Mycobacterium paratuberculosis, Mycobacterium ulcerans, Mycobacterium marinum, Mycobacterium smegmatis, Mycobacterium intracellulare, Mycobacterium xenopi, Mycobacterium chelonei, Mycobacterium fortuitum, Mycobacterium farcinogenes, Mycobacterium flavum, Mycobacterium haemophitum, Mycobacterium kansasii, Mycobacterium phlei, Mycobacterium scrofulaceum, Mycobacterium senegalense, Mycobacterium simiae, Mycobacterium thermoresistible*, and *Mycobacterium xenopi.*

17. The composition of claim 6, wherein said polypeptides are isolated from at least one *Mycobacterium* selected from the group consisting of *Mycobacterium tuberculosis, Mycobacterium avium, Mycobacterium microti, Mycobacterium leprae, Mycobacterium lepraemurium, Mycobacterium paratuberculosis, Mycobacterium ulcerans, Mycobacterium marinum, Mycobacterium smegmatis, Mycobacterium intracellulare, Mycobacterium xenopi, Mycobacterium chelonei, Mycobacterium fortuitum, Mycobacterium farcinogenes, Mycobacterium flavum, Mycobacterium haemophitum, Mycobacterium kansasii, Mycobacterium phlei, Mycobacterium scrofulaceum, Mycobacterium senegalense, Mycobacterium simiae, Mycobacterium thermoresistible*, and *Mycobacterium xenopi.*

18. The composition of claim 5, that further comprises the 38 kilodalton antigen of *M. tuberculosis.*

19. The composition of claim 6, that further comprises the 38 kilodalton antigen of *M. tuberculosis.*

20. The isolated polypeptide of claim 2, wherein the polypeptide has a molecular weight of from 5 to 100 kilodaltons.

21. The isolated polypeptide of claim 2, wherein the polypeptide has a molecular weight of from 28 to 65 kilodaltons.

* * * * *